US008636703B2

(12) United States Patent
Foshee et al.

(10) Patent No.: US 8,636,703 B2
(45) Date of Patent: Jan. 28, 2014

(54) NEEDLE SAFETY MECHANISM

(76) Inventors: David L. Foshee, Apex, NC (US);
Theodore J. Mosler, Raleigh, NC (US);
Bryan J. Peters, Raleigh, NC (US);
Todd M. Korogi, Raleigh, NC (US);
Nicholas J. Jardine, Cary, NC (US)

( * ) Notice: Subject to any disclaimer, the term of this patent is extended or adjusted under 35 U.S.C. 154(b) by 631 days.

(21) Appl. No.: 12/743,748

(22) PCT Filed: Nov. 19, 2008

(86) PCT No.: PCT/US2008/084055
§ 371 (c)(1),
(2), (4) Date: Mar. 7, 2011

(87) PCT Pub. No.: WO2009/067531
PCT Pub. Date: May 28, 2009

(65) Prior Publication Data
US 2011/0152832 A1    Jun. 23, 2011

Related U.S. Application Data

(63) Continuation-in-part of application No. PCT/US2008/073870, filed on Aug. 21, 2008.

(60) Provisional application No. 61/003,676, filed on Nov. 19, 2007.

(51) Int. Cl.
*A61M 5/32* (2006.01)

(52) U.S. Cl.
USPC ............ 604/198; 604/110; 604/192; 128/919

(58) Field of Classification Search
USPC ........................... 604/198, 110, 192; 128/919
See application file for complete search history.

(56) References Cited

U.S. PATENT DOCUMENTS 4,795,443 A    1/1989   Permenter et al.
4,846,811 A *  7/1989   Vanderhoof ................... 604/263
(Continued)

FOREIGN PATENT DOCUMENTS

EP      0 549 382 A1      6/1993
WO      WO 03 086514 A1   10/2003

OTHER PUBLICATIONS

The International Bureau of WIPO, International Preliminary Report on Patentability and Written Opinion of the International Search Authority, date May 25, 2010.

*Primary Examiner* — Kevin C Sirmons
*Assistant Examiner* — Edelmira Bosques
(74) *Attorney, Agent, or Firm* — Christopher J. Knors; Moore & Van Allen PLLC

(57) ABSTRACT

A syringe needle safety apparatus comprising a syringe barrel having an open end and an opposite end adapted for a needle and a needle safety cover displaceable between a un-deployed state wherein the cover is constrained and the needle exposed, and a deployed state wherein the cover covers at least the needle tip. A plunger is slidably engaged in the syringe barrel and at least one element secures the needle safety cover in the un-deployed state. Biasing means urge the needle safety cover from the un-deployed state to the deployed state, and a housing is coupled to the opposite end of the syringe barrel, the housing comprising a corresponding securing member and a deformable member, the deformable member releasing the at least one element from the corresponding securing member upon receiving a releasing force via the plunger. During deployment, the needle safety mechanism provides for the needle safety cover to avoid contact with the needle, reducing or eliminating blood contact.

13 Claims, 28 Drawing Sheets

(56) References Cited

U.S. PATENT DOCUMENTS

| | | |
|---|---|---|
| 4,994,046 A | 2/1991 | Wesson et al. |
| 5,152,751 A | 10/1992 | Kozlowski |
| 5,215,534 A | 6/1993 | De Harde et al. |
| 5,312,372 A | 5/1994 | DeHarde et al. |
| 5,466,223 A | 11/1995 | Bressler et al. |
| 5,681,291 A | 10/1997 | Galli |
| 7,001,363 B2 | 2/2006 | Ferguson et al. |
| 7,077,824 B2 | 7/2006 | Meyer |
| 2003/0191438 A1 | 10/2003 | Ferguson et al. |
| 2005/0159706 A1* | 7/2005 | Wilkinson et al. ............ 604/110 |

* cited by examiner

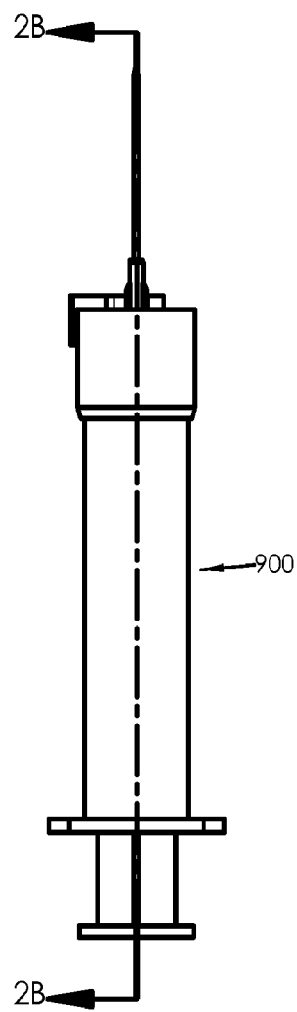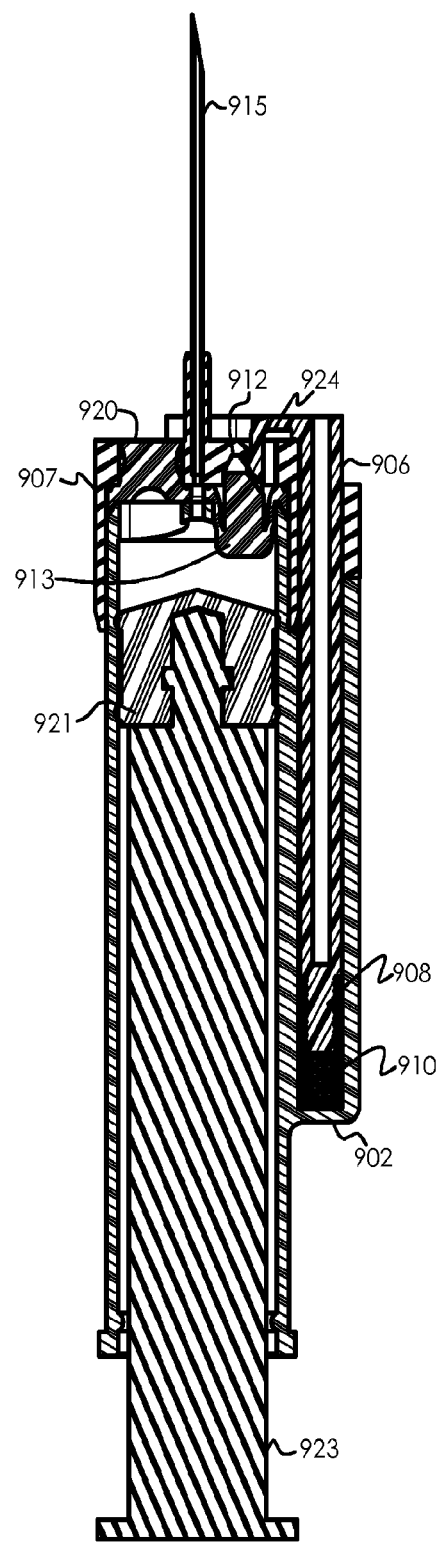
FIG. 2A
FIG. 2B

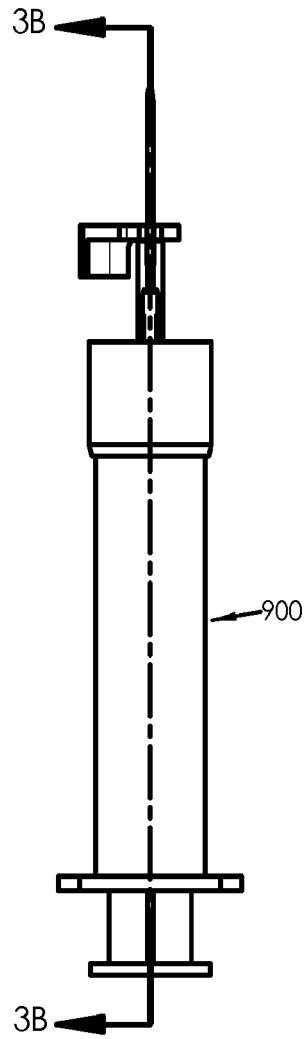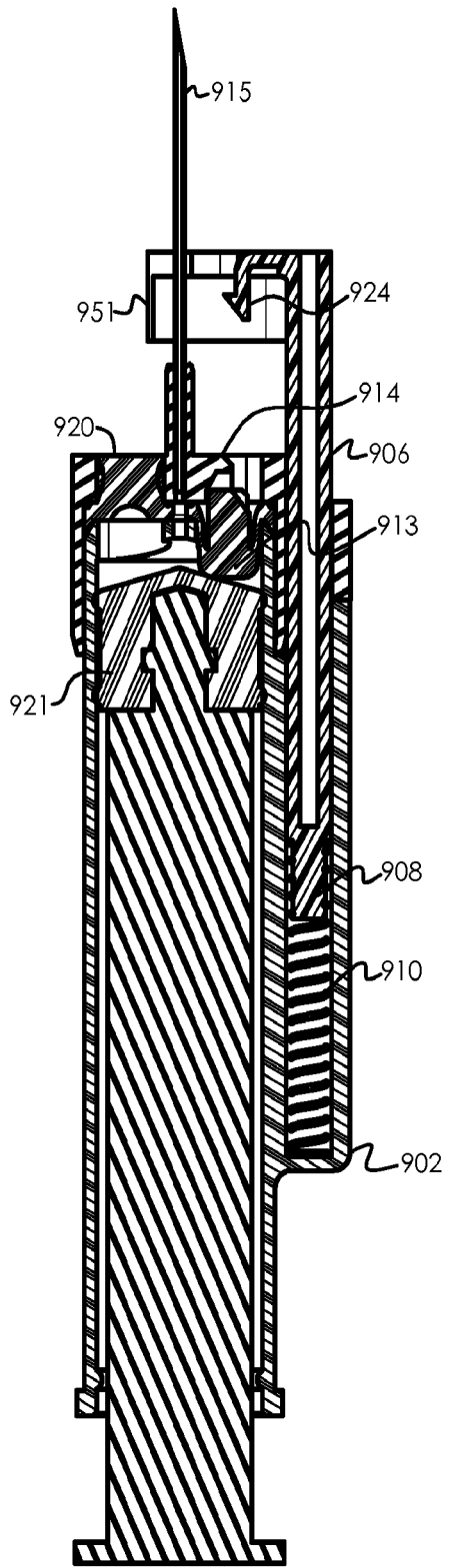
FIG. 3A
FIG. 3B

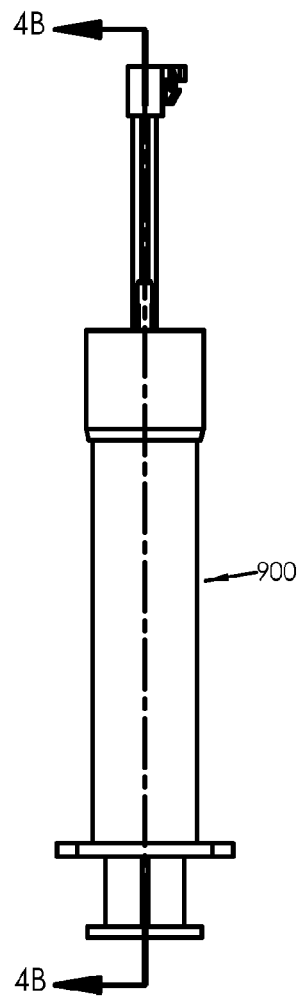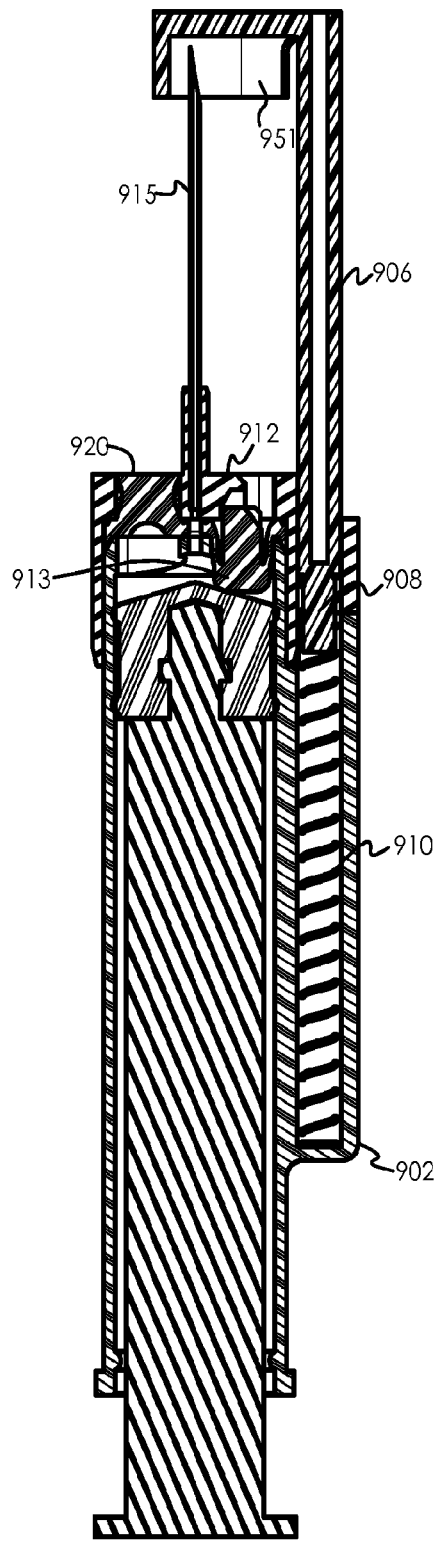
FIG. 4A
FIG. 4B

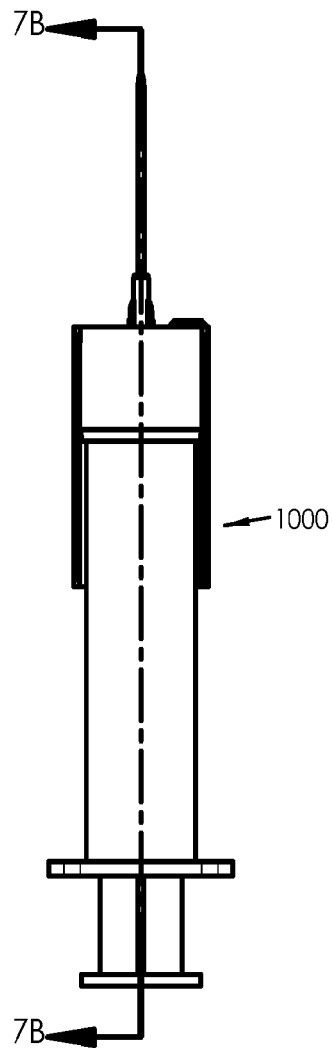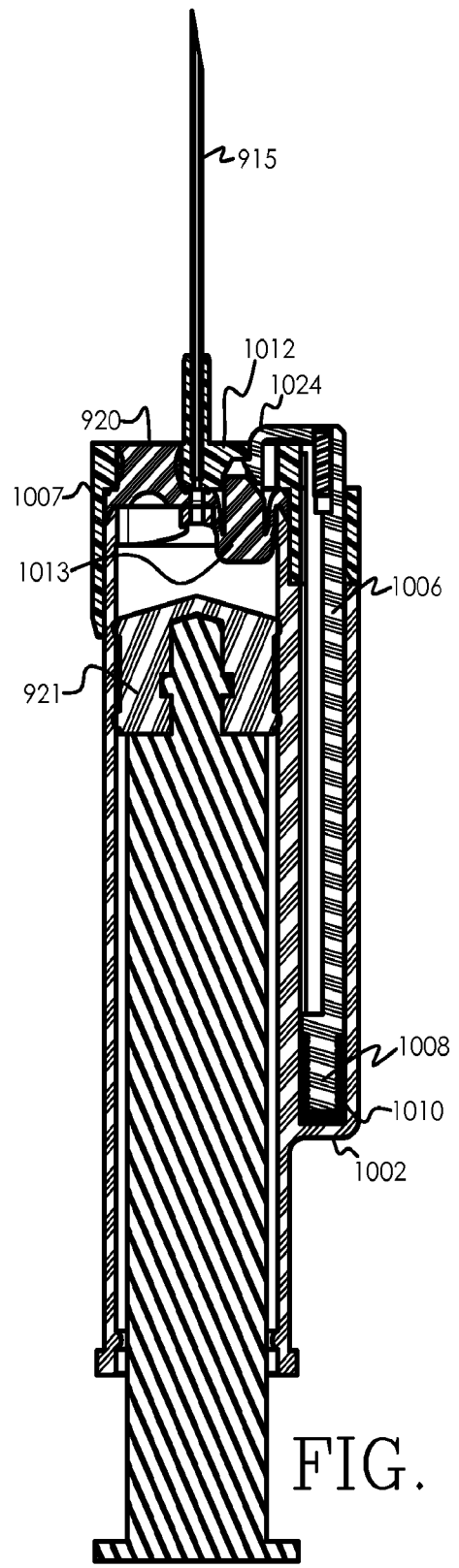
FIG. 7A
FIG. 7B

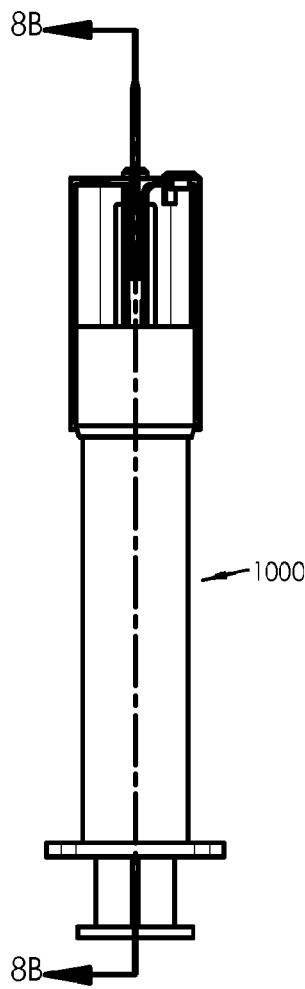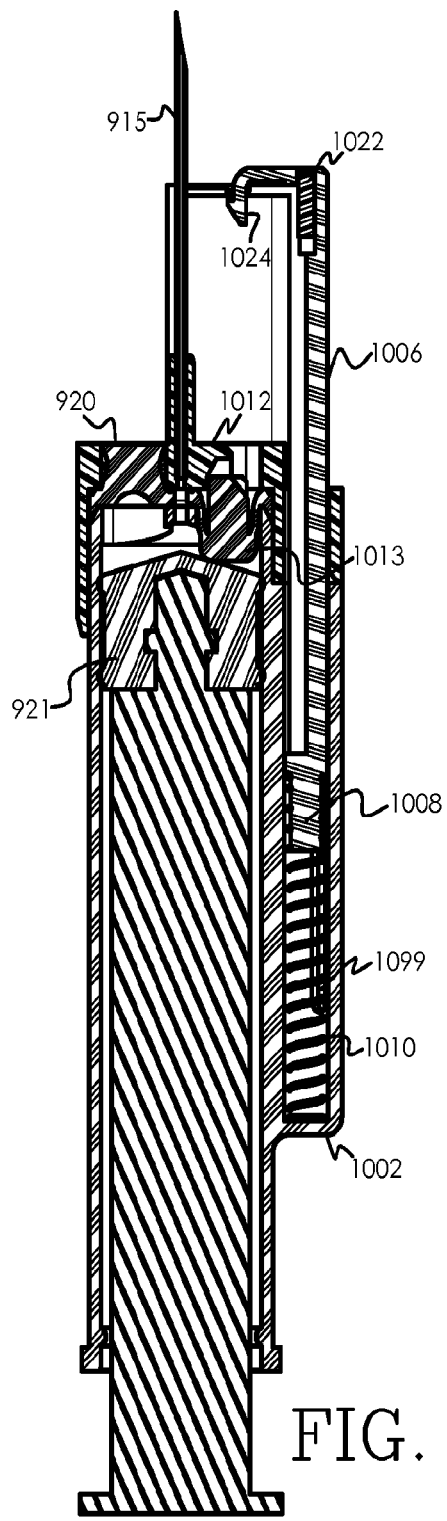
FIG. 8A
FIG. 8B

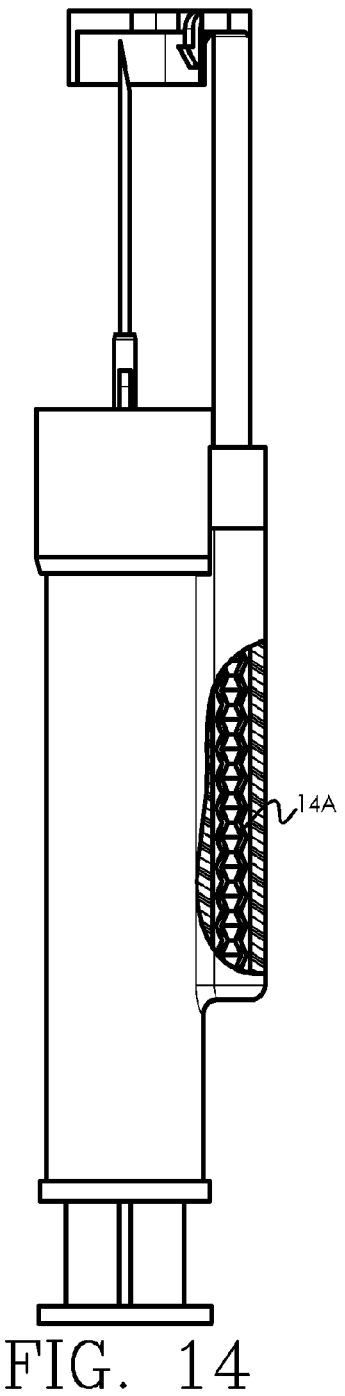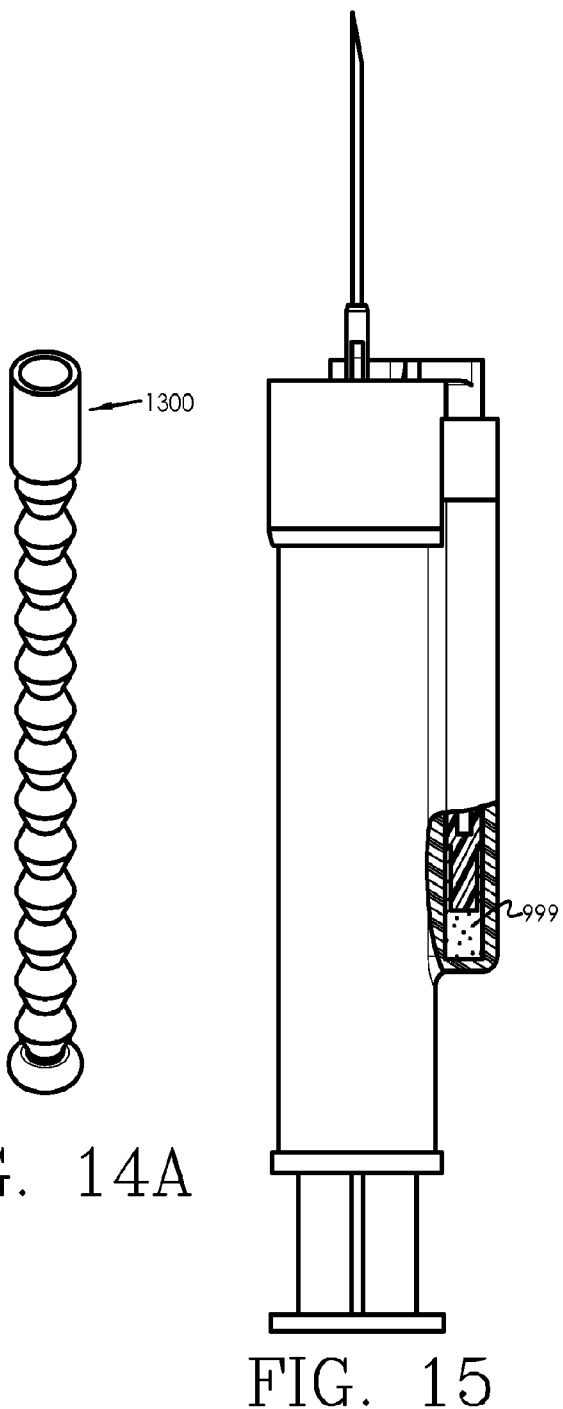
FIG. 14
FIG. 14A
FIG. 15

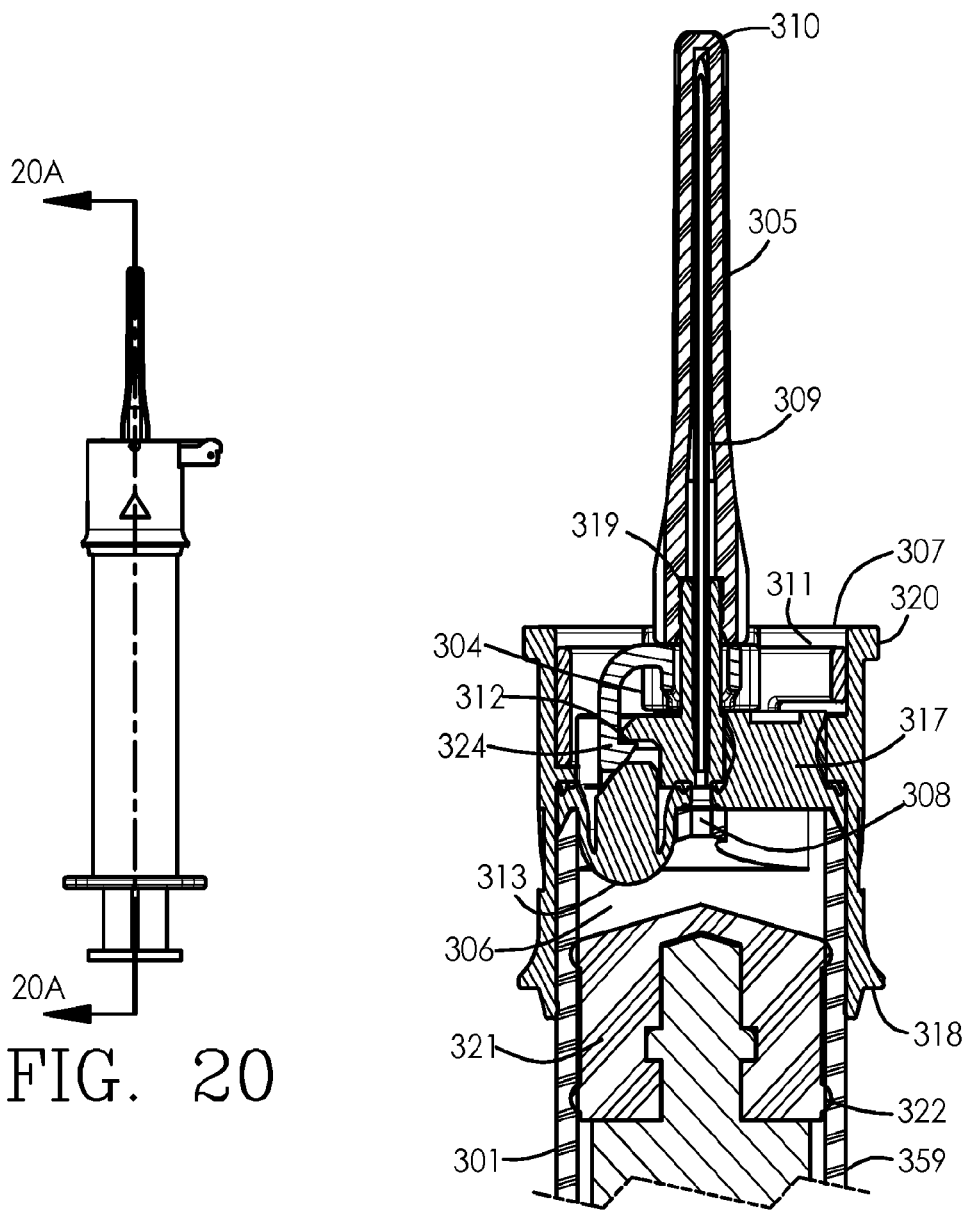
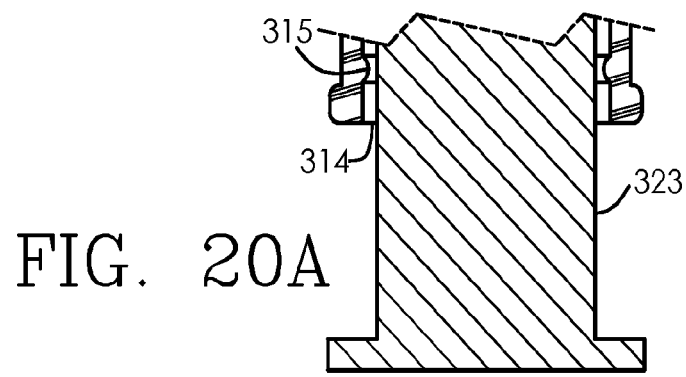
FIG. 20
FIG. 20A

NEEDLE SAFETY MECHANISM

CROSS-REFERENCE TO RELATED APPLICATIONS

This application is filed under the provisions of 35 U.S.C. §371 and claims the priority of International Patent Application No. PCT/US2008/084055, filed on 19 Nov. 2008 entitled "Needle Safety Mechanism" in the name of David L. Foshee, et al., which claims priority of Patent Application Nos. PCT/US2008/073870, filed on 21 Aug. 2008 and U.S. Provisional Patent Application No. 61/003,676 filed on 19 Nov. 2007, all of which are hereby incorporated by reference herein in their entirety.

TECHNICAL FIELD

This disclosure relates to a needle safety mechanism and a syringe comprising same.

BACKGROUND

Some needle safety mechanisms use a trigger or other structure that actuates a spring to retract the needle into the barrel or to urge a cover over the needle. Such retraction and extending cover systems have significant limitations, including inadvertent exposure to blood by the user from blood spray or blood "back-splash" during the deployment process. Furthermore, contact of the needle safety mechanism with the needle during deployment, for example, covers with guide holes riding the needle shank, may cause significant blood-born exposures by spraying. Another limitation is that the trigger is often not adequately protected from inadvertent actuation. Inadvertent actuation may result in needle safety mechanism deployment before administration is complete, which can render the syringe un-usable and/or waste expensive medication.

Consequently, there is a need for a needle safety mechanism that protects users from both needlesticks and contact with blood, and improves the simplicity and dependability of the deployment process for users.

SUMMARY

The foregoing and other advantages and features are provided in an apparatus which comprises a syringe barrel having an open end and an opposite end adapted for a needle and a needle safety cover displaceable between a un-deployed state wherein the needle safety cover is constrained and the needle exposed, and a deployed state wherein the needle safety cover covers at least the needle tip. A plunger is slidably engaged in the syringe barrel and at least one element secures the needle safety cover in the un-deployed state. Biasing means urge the needle safety cover from the un-deployed state to the deployed state, and a housing coupled to the syringe barrel comprises a corresponding securing member and a deformable member, the deformable member releasing the at least one element from the corresponding securing member upon receiving a releasing force via the plunger. During deployment, the needle safety mechanism provides for the needle safety cover to avoid contact with the needle, reducing or eliminating blood contact.

In another embodiment, a method of reducing or eliminating blood contact is provided. The method comprises providing syringe with an open end and needle safety mechanism deploying a needle safety cover from un-deployed state wherein the needle safety cover is constrained and the needle exposed, to a deployed state wherein the needle safety cover covers at least the needle tip. The needle safety mechanism comprises a plunger slidably engaged in the barrel of the syringe and at least one element securing the needle safety cover in the un-deployed state. Biasing means urges the needle safety cover from the un-deployed state to the deployed state. A housing is coupled to the syringe barrel, the housing comprising a corresponding securing member and a deformable member, the deformable member releasing the at least one element from the securing member upon receiving a releasing force via the plunger. The method avoids contact of the needle safety cover with the needle during deployment reducing or eliminating blood contact.

BRIEF DESCRIPTION OF THE FIGURES

FIG. 2A and FIG. 2B are sectional plane and cross-sectional views, respectively, of an embodiment disclosed herein in an initial/loaded state before the safety mechanism is released.

FIG. 3A and FIG. 3B are sectional plane and cross-sectional views, respectively, of the embodiment of FIG. 2A in an intermediate, deployed state.

FIG. 4A and FIG. 4B are sectional plane and cross-sectional views, respectively, of the embodiment of FIG. 2A in final state.

FIG. 7A and FIG. 7B are sectional plane and cross-sectional views, respectively, of an embodiment disclosed herein in an initial/loaded state.

FIG. 8A and FIG. 8B are sectional plane and cross-sectional views, respectively, of the embodiment of FIG. 7A in an intermediate, deployed state.

FIG. 13' and FIG. 13A' are sectional plane and cross-sectional views, respectively, of an embodiment of FIG. 7A without an access port.

FIG. 14 is a profile view of an embodiment disclosed herein with a collapsible, elastomeric compression spring for deploying the safety mechanism.

FIG. 14A is a perspective view of a collapsible elastomeric compression spring of FIG. 14.

FIG. 15 is a profile view of an embodiment disclosed herein with compressed air for deploying the safety mechanism.

FIGS. 19-19A and 20-20A are sectional plane and partial cross-sectional views, respectively, of a needle-stick safety mechanism embodiment with needle cap.

DETAILED DESCRIPTION

Figure 1:
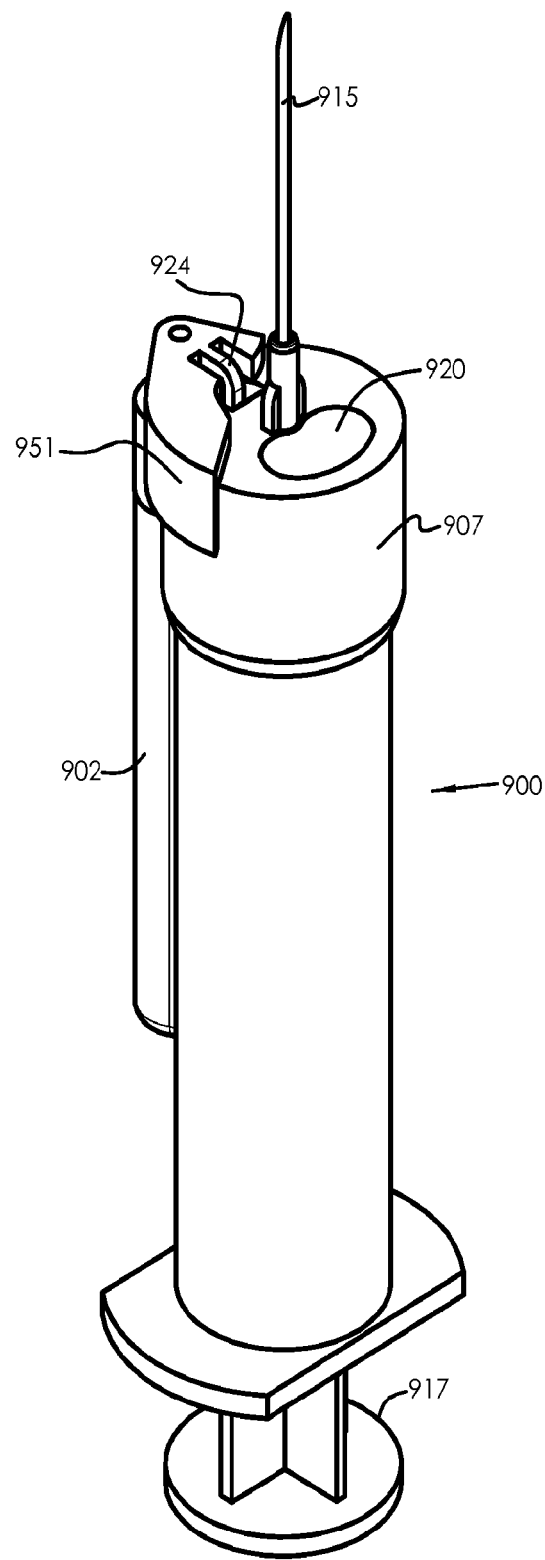
FIG. 1 is a perspective view of an embodiment of the present invention.

Disclosed herein is needle safety mechanism and devices incorporating the same. The needle safety mechanism is adaptable to other devices, for example fluid transfer devices that provide for mixing and transferring.

The phrase "vertical motion" is regarded as non-limiting and generally refers to the direction parallel to the axis of syringe barrel, more specifically, towards the needle of the syringe parallel to the syringe barrel axis.

The phrase "avoids contacting the needle" and its grammatical equivalents refers to substantially no physical contact of the needle safety cover with the needle, up to and until the needle safety cover has come to rest from its deployment. For example, the needle safety cover does not ride the needle of the syringe during deployment or use the needle to stop its motion during deployment. In this way, contact with blood by the user is eliminated or reduced.

In one aspect, the apparatus is adaptable to a transfer device suitable for mixing and transferring materials. The transfer device comprises a housing having open ends, a container accessing member having at least one fluid conduit therethrough, the container accessing member extending generally outwardly from one open end of the housing. The housing also comprises a syringe accessing member having at least one fluid conduit therethrough, the syringe accessing member extending generally towards the other open end of the housing, the syringe accessing member and the container accessing member in fluid communication therewith. The device further comprises receiving means within the housing, the receiving means configured to receive a dispensing member of the fluid delivery device. The access device is configured to provide an interface between the contents of a container and the syringe. The access device is configured such that the syringe and the container may reversibly and sealably mate to the access device and be in fluid communication therewith.

The syringe may be adaptable to the transfer device, whereby the syringe comprises at least one access port capable of receiving the syringe accessing member of the access housing. The access port facilitates drawing fluid in through the bypass fluid channel of the syringe accessing member and delivery of the fluid to the syringe, bypassing the needle of the syringe. The access port may be a 2-way port, allowing fluid to be transferred from the syringe to the container. While the embodiments described herein depict an access port as part of the syringe, it is appreciated that the needle safety mechanism disclosed herein may be employed without the access port and therefore, the access port is optional in this regard.

The syringe comprises barrel having an open end and a needle at the opposite end, a plunger having a first end and a second end; the first end which may have gripping means for ergonomic control and a second end that may have an elastomeric stopper. Attachment means may be provided proximal to or integrated with the second end of the stopper for attaching a syringe stopper. The syringe stopper may have any number of contiguous sealing elements about its outer portion perimeter for creating a slidable seal within the syringe barrel. The syringe stopper may be constructed of any of a variety of materials which are biocompatible, sterilizable, and able to withstand exposure to the intended fluid media for the system. These materials preferably are resilient or reasonably deformable and may include, but are not limited to, elastomers such as rubber, silicone and thermoplastic or thermoset elastomers. In another aspect, the syringe and stopper constitute a two-piece syringe, whereas an elastomeric stopper is not employed.

Access Port

With regard to the syringe adaptable to a transfer device as herein described, an access port may be employed. The access port provides fluid communication between the fluid delivery device accessing member and the fluid delivery device. The access port is preferably re-sealable. In one aspect, the access port is a self-closing, sealable access port positioned at the distal end of the fluid delivery device adjacent the dispensing member such that during transfer and/or mixing, fluid is substantially diverted from traversing the dispensing member. The sealable access port may be comprised of sealing means, a pre-slit septum portion and a thin membrane section, or combinations thereof. In one aspect, the sealable access port is a pre-slit septum extruded with a general parabola shape, a duck-bill shape, or combination of similar geometries, which may be pre-slitted for re-sealable and re-useable access. In one aspect, the access port is a "duckbill" check valve. In another aspect, the access port is a pre-slit septum with a parabola-like extrusion that may further function as a check valve.

In one aspect, the sealable access port comprises or is integral with a deformable membrane. The deformable membrane, as further described herein, generally provides for substantially fluid-sealed operation and provides user-activated or passive activation of a needle-stick safety mechanism. The access port may be any of a variety of materials which are biocompatible, sterilizable, durable, and able to withstand exposure to the intended fluid media for the system. These materials preferably are resilient or reversibly deformable and may include but are not limited to elastomers such thermoplastic elastomers or thermoset elastomers. Exemplary materials useful for the access port include, for example, latex-free rubber, silicones, and polyurethanes.

Syringe Housing

The syringe housing (also referred to herein as the "lower housing") comprises a suspended portion across the inner diameter thereof. The suspended portion comprises a deformable section that provides, in one aspect, communication between the transfer device and the needle stick safety mechanism for activation. The suspended portion may be an elastomeric membrane, which may function to maintain a clean, leak-free syringe. The lower housing also may provide for attachment of the fluid delivery device with the access device. In the case of a needle-stick safety mechanism, the lower housing may provide a corresponding securing means for a needle safety cover coupled to a stored energy bias. The lower housing preferably does not hinder the fluid path into the fluid delivery device.

The lower housing comprises attachment means allowing for sealable joining to a fluid delivery device, an elastomeric portion to create a hermetic seal upon joining; attachment members for substantial joining of a dispensing member and an opening or set of openings for allowing fluid to pass through the dispensing member and access to the access port of the fluid delivery device. In another aspect, the lower housing also may provide for activation of the needle safety mechaism.

Needle-Stick Safety Mechanisms

A conventional needle cap may provide some level of protection for the user from needle-stick prior to injection into a patient. Another level of needle-stick safety may be implemented to the syringe as described herein. For example, once the device has been used, a needle-stick safety mechanism (also referred to herein as "needle safety mechanism") may passively deploy a covering device or mechanism that covers at least the needle-tip. In another aspect, the needle-stick safety mechanism may be activated by the user to deploy a covering device or mechanism that covers at least the needle-tip and protects the user and others from accidental needle sticks. Additionally, by housing the needle assembly within the vial access device and assembling the device with this needle-stick safety mechanism during manufacturing provides greater safeguards during assembly. Passive needle-stick safety mechanisms may include, but are not limited to, an internal end-of-stroke needle-stick protection release mechanism, defined herein, as well as known needle protection devices, both passive and active (e.g., button, slides, door, etc.).

In one aspect, the needle safety cover comprises at least one element securing the needle cover in the un-deployed state, in part, that mates with mating securing means within the syringe housing or in proximity to the syringe distal end. When a releasing force is applied, the at least one element is released from the securing member releasing stored energy and urging the needle safety cover. External force applied directly or indirectly to the at least one element releases the needle safety cover of the safety mechanism, which is acted on by stored energy means, sending the needle safety cover toward the needle tip. The at least one element securing the needle cover in the un-deployed state may be integral with the needle safety cover.

In another aspect, the needle safety cover component comprises an open inner portion, an outer portion, a first end and a second end; the outer portion having an attachment means for a spring; the first end having one or more latching means. The needle safety cover may include a guide hole for sliding along a needle. When the needle safety cover guide hole passes the needle tip, the spring, having been assembled off-center with the needle centerline, moves the needle-tip cover off-center and onto the needle tip. The spring may be of a traditional metal wire form, or be made of any material including, but not limited to an elastomer or plastic, a bellows type, a helical coil with flat ends for mounting, a double helix type, and the like, or may comprise one or more materials. In one aspect, a guide hole in the needle safety cover is not preferred and is to be avoided to eliminate or reduce blood spray during deployment.

In one aspect, the needle stick safety mechanism may comprise a torsional member loaded to provide stored energy that is released at the end of the plunger stroke. Torsional members may be, but are not limited to, torsion springs, leaf springs or tension springs coupled such that when the needle-stick safety mechanism is released, the torsional spring or springs will force its coupled members from a collapsed configuration to an extended configuration. Torsional members may be steel forms, plastic forms or elastomeric forms.

The syringe and needle safety mechanism combination described above may also include a standard needle cap covering needle when the syringe is in the un-deployed state, and can be distributed and packaged in such configuration.

Use of the apparatus as herein described is as follows. Prior to use of the syringe with needle safety mechanism and optional needle cap, the syringe may be filled with fluid by a transfer device through an access port without using the plunger or the needle for fluid transfer as described above. Alternatively, the syringe may be filled by a conventional method using the needle. After fluid transfer into the syringe barrel using the transfer device and prior to first use, the optional needle cap is removed, and the otherwise unused needle is inserted in the subject and the fluid is administered in a conventional manner, for example, by the application of digital pressure on the portion of the plunger extending from the syringe barrel while supporting the finger flanges. After the fluid is administered, and after the needle has been removed from the subject, the method of preventing or reducing blood contact comprises providing syringe with an open end and needle safety mechanism deploying a needle safety cover from un-deployed state wherein the cover is constrained and the needle exposed, to a deployed state wherein the cover covers at least the needle tip. The needle safety mechanism comprises a plunger slidably engaged in the barrel of the syringe; and at least one element securing the needle safety cover in the un-deployed state. Biasing means urge the needle safety cover from the un-deployed state to the deployed state. A housing is coupled to the syringe barrel opposite the open end, the housing comprising a corresponding securing member and a deformable member, the deformable member releasing the at least one element from the securing member upon contact with the actuation end of the plunger, avoiding contact of the needle safety cover with the needle during deployment.

Referring now to the drawings, various illustrative embodiments will be described.

As shown in FIGS. 1-6, device (900) comprises needle safety cover (951) is adapted to arm (906) contained in external housing (902). Needle safety cover at least partially surrounds the syringe barrel when in the un-deployed state. The needle includes latch (924) configured to engage latch shelf (912) of the housing. When the latch is engaged with the latch shelf the needle (915) is exposed and the needle safety cover is positioned adjacent the housing. In one aspect, release of the latch from the latch shelf is accomplished by the plunger (923) at its end-of-stroke. As shown by way of example in FIG. 2B, the syringe plunger, which may include an elastomeric stopper (921) comprising a resilient material, for example rubber, having a generally conically shaped distal end, is at its end-of-stroke in proximity to deformable member (913) of housing (907). When the plunger is further advanced against the deformable member of the housing, the latch of the needle safety cover is released from the latch shelf of the housing, activating the stored-energy bias (910) in the external housing deploying the needle safety cover. The sequence of un-deployed, during deployment and deployed states are shown in FIGS. 5A-5C. The syringe of FIG. 2A may alternatively have a plunger without the elastomeric stopper (not shown) and without access port (920) without departing from the above deployment mechanism. In one embodiment, during deployment, the shield is urged toward the needle tip and the shield and arm rotates about the axis of external housing (902) to position the needle safety cover over the needle tip avoiding contact with the needle and thereby preventing or eliminating blood contact.

In one aspect, the needle safety mechanism permits the activation of needle safety cover (951) without placing the user in proximity to the distal end of needle. This is accomplished by providing at the plunger's end-of-stroke the activation of the needle safety mechanism. The needle safety mechanism may be configured such that the user tactilely senses contact with the activating means (e.g., deformable member), whereby an additional force or "releasing force" applied by the user on the plunger would then deploy the needle safety cover. In this way, the needle may be used more than once before deploying the safety mechanism, if desired.

With reference to FIG. 2B, external housing (902) includes bias means (910) in a stored energy state for deploying needle safety mechanism. By way of illustrative example, bias means comprising a helical spring will be described, however, the use of a helical spring is not limiting, and other stored energy means may be used, for example, compressed elastomeric spring, compressed fluid, elastomeric tension bands, magnets, ect. Thus, external housing includes helical spring bias (910) in a compressed condition. Arm (906) is coupled at distal end (908) end to the helical spring and to the needle safety cover (951) at the other end. Needle safety cover latch and housing latch shelf maintain helical spring in a compressed, energy stored condition. Other latching means may be employed, for example, ball and socket, and the like.

Figure 5A:
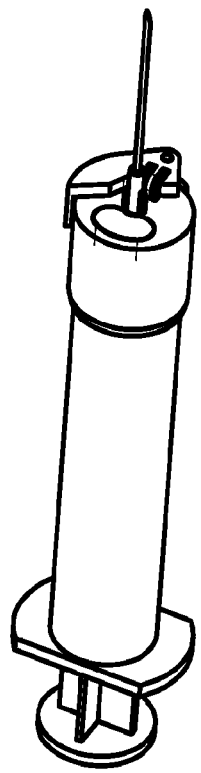
FIG. 5A, FIG. 5B and FIG. 5C are prospective views of the embodiment of FIG. 2A in the initial/loaded state, the intermediate, deployed state, and the final state, respectively.
Figure 5B:
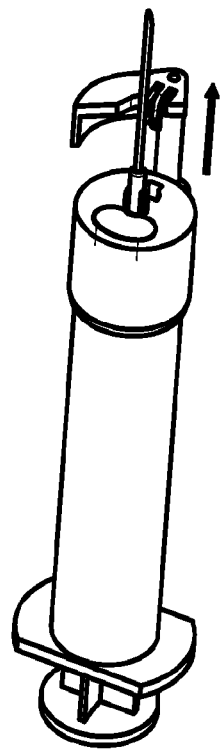
Figure 5C:
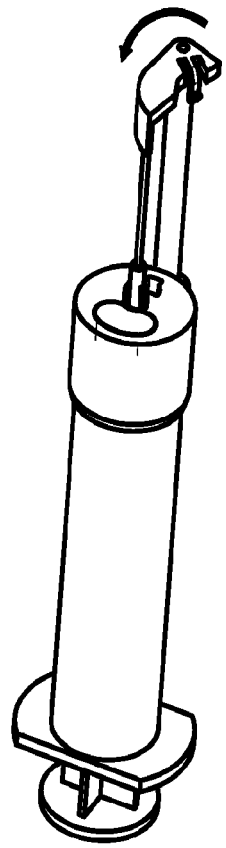
Figures 6, 6A, 6B:
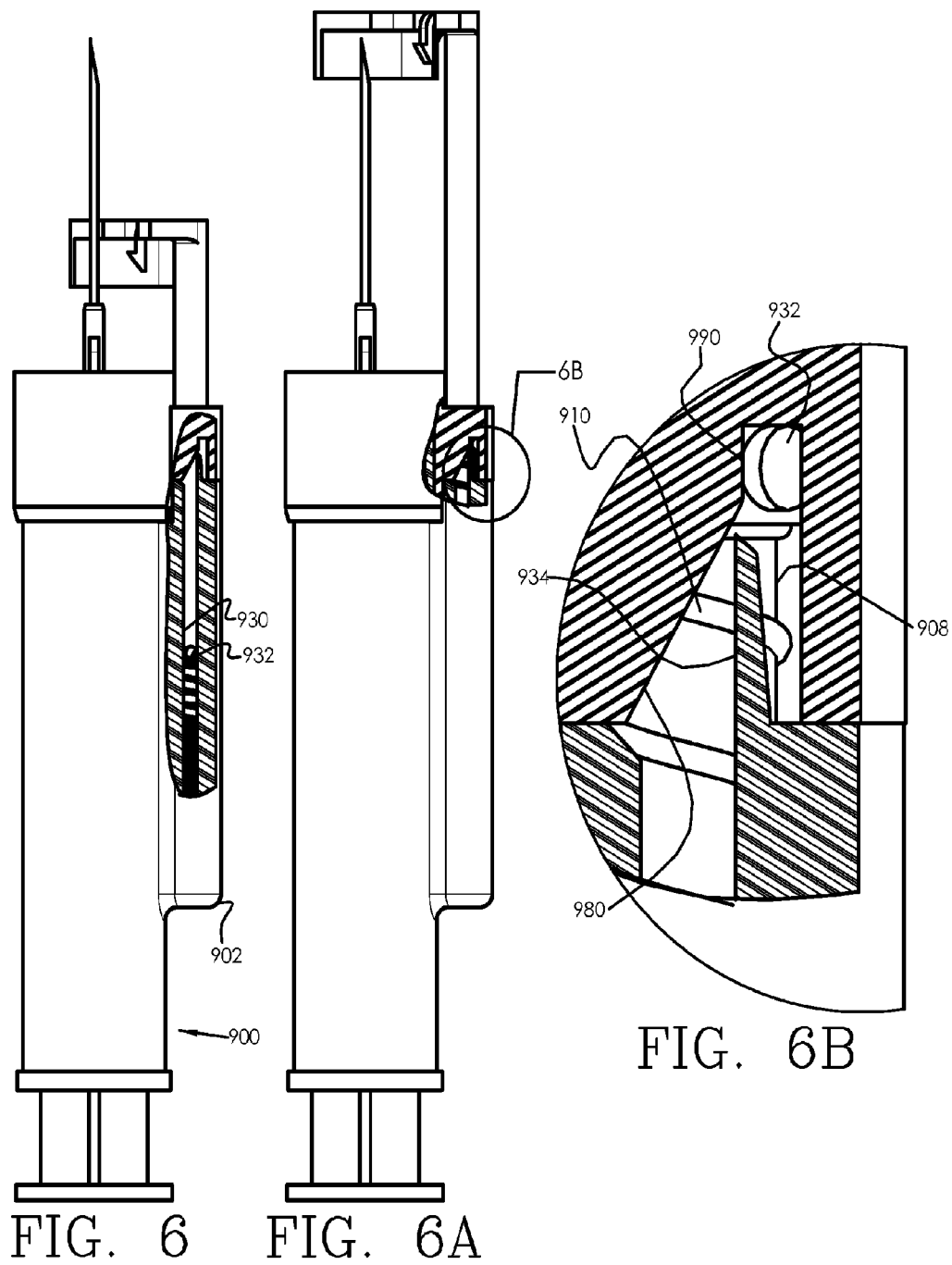
FIG. 6 is a profile view with a partial section view of the embodiment of FIG. 2A in the intermediate, deployed state showing a cam/follower mechanism providing an end-of stroke twisting motion of the safety mechanism.
FIG. 6A and FIG. 6B are profile and partial detail section views of the embodiment of FIG. 2A in the final state showing the cam/follower mechanism in its final position.
Figures 9A, 9B:
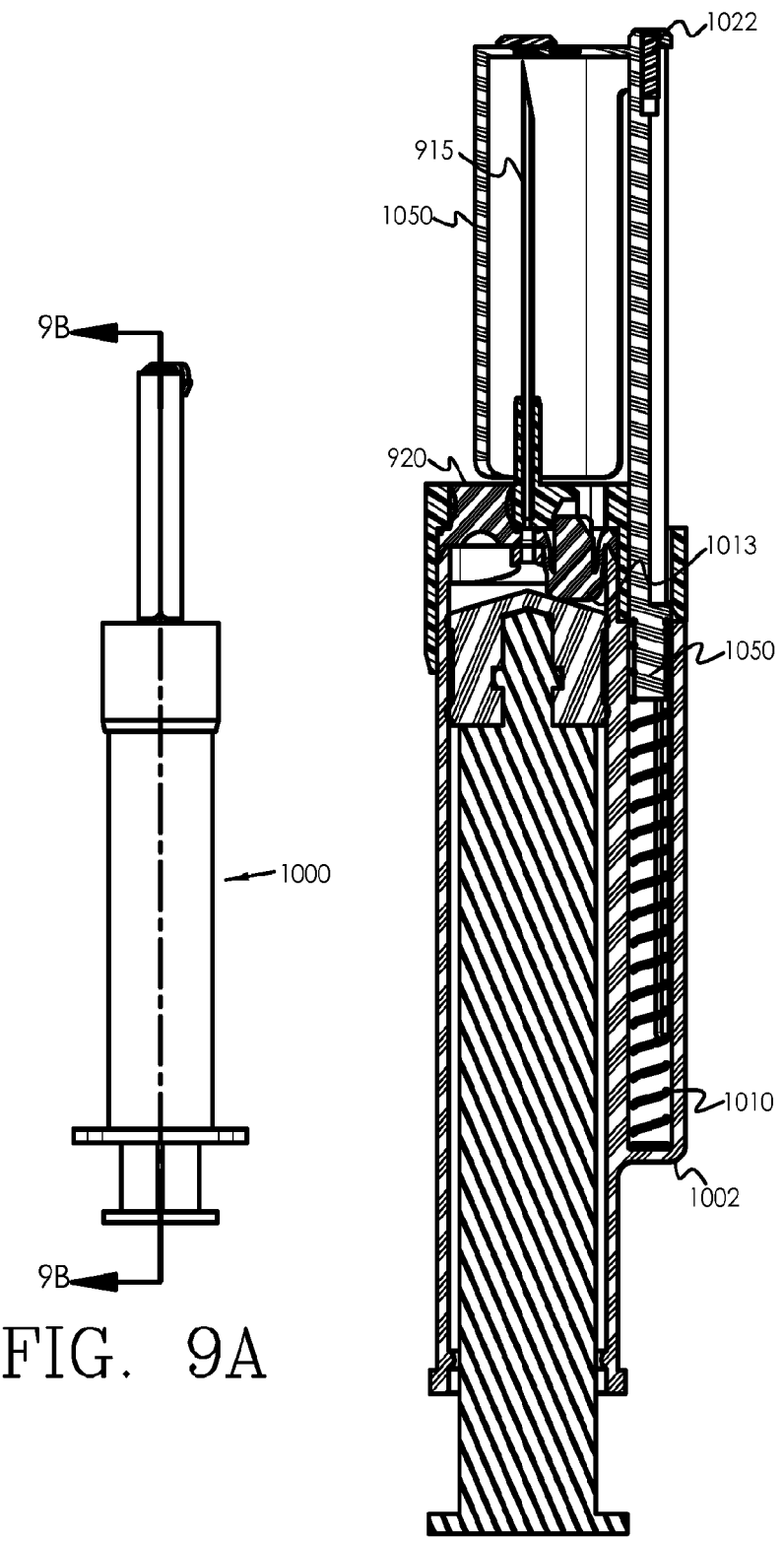
FIG. 9A and FIG. 9B are sectional plane and cross-sectional views, respectively, of the embodiment of FIG. 7A in final state.
Figure 10A:
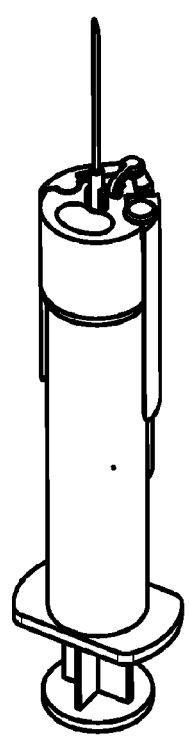
FIG. 10A, FIG. 10B and FIG. 10C are prospective views of the embodiment of FIG. 7A in the initial/loaded state, the intermediate, deployed state, and the final state, respectively.
Figure 10B:
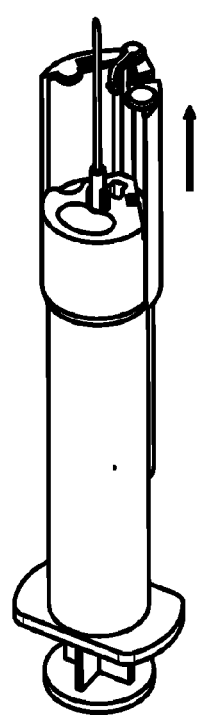
Figure 10C:
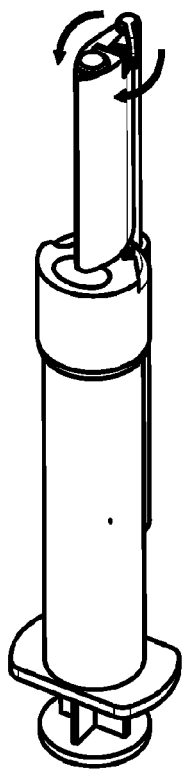
Figures 11, 11A:
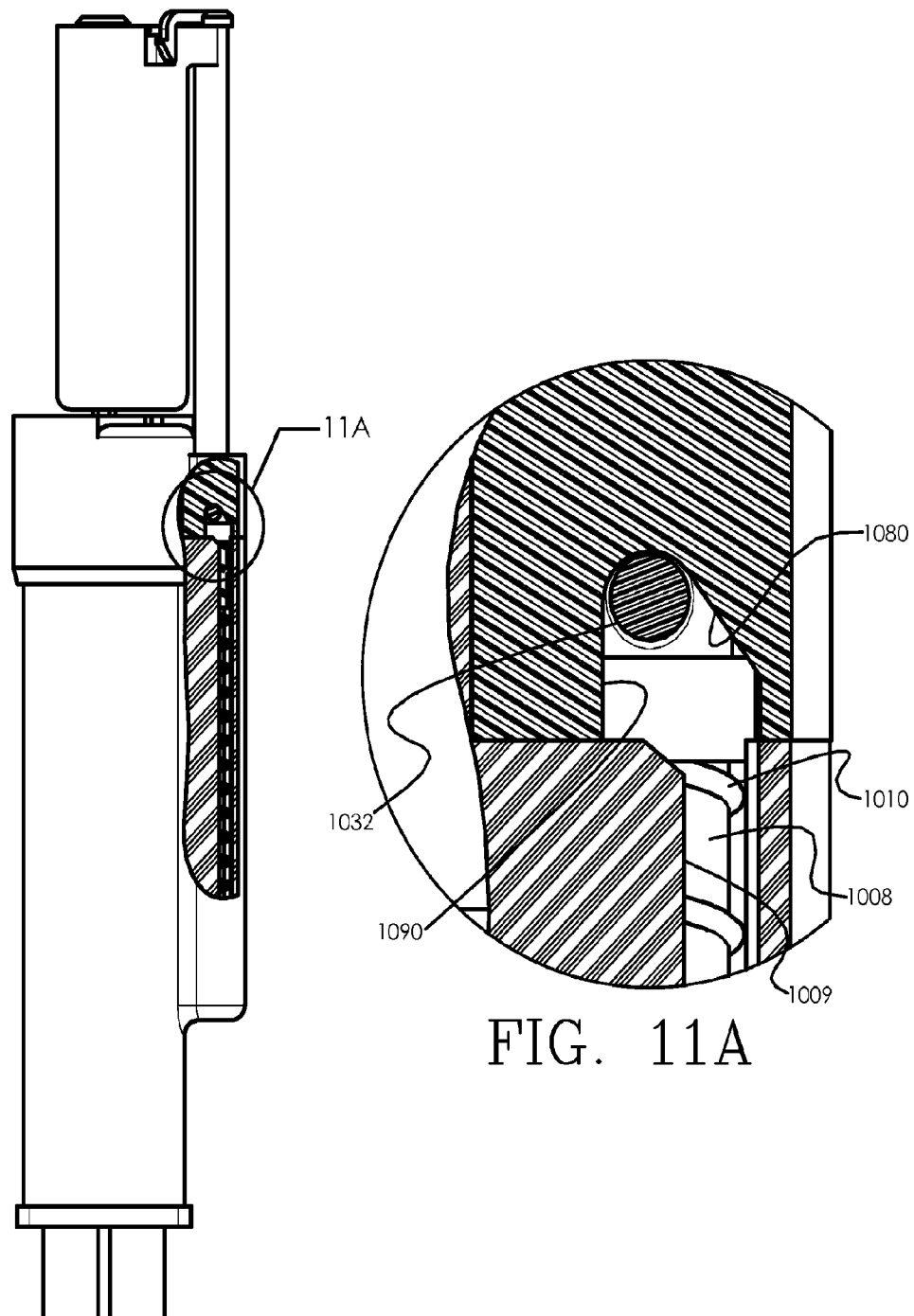
FIG. 11 and FIG. 11A are profile and partial detail section views of the embodiment of FIG. 7A in the final state showing a cam/follower mechanism in its final position.

In one aspect, as shown in the sequence show in FIGS. 5A-C, needle safety cover initially is in axial alignment with syringe barrel and then needle safety cover rotates about the syringe barrel axis. As shown in FIGS. 6-6B, further along deployment, follower (932) of arm reaches proximity of external housing open end, and cam of external housing provides for the needle safety cover to rotate to a position in proximity to needle tip. In its deployed extended condition, a portion of the needle safety cover will be slightly beyond needle tip to prevent later inadvertent contact with needle tip. FIG. 6B is a detail view of inclined surface (980) showing the cam follower (932) in its final position. Follower is locked rotationally by vertical surface (990) beyond inclined surface (980) with respect to travel. A second locking mechanism (934) prevents the follower from returning down the cam surface. Locking mechanism (934) may be deflectable by follower (932), or alternatively, provide interference to otherwise prevent or reduce arm (906) from retracting after deployment.

Figures 12, 12A:
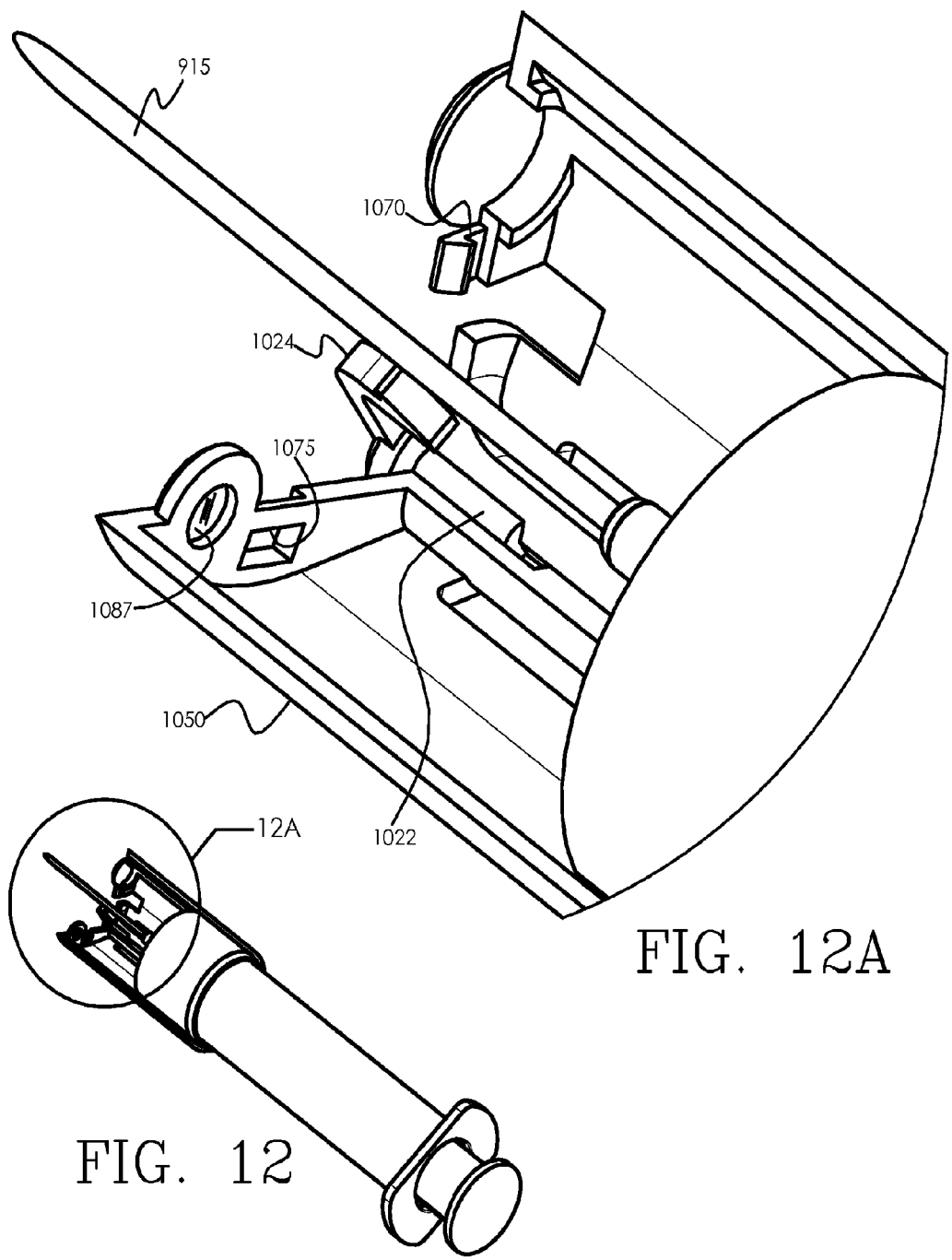
FIGS. 12 and 12A are profile and partial detail section views of the embodiment of FIG. 7A showing a snap and latch locking mechanism.

An alternative embodiment which may be employed to implement the needle safety cover structure necessary to essentially encase the needle, can be best exemplified by reference to FIGS. 7-12A. Thus, device (1000) comprises a pair of concave shields are each coupled to arm (1006) forming a hinge (1022) at least partially surrounding syringe barrel in the un-deployed state. Upon deployment, by deformable member (1013), the pair of concave shields (1050) is urged together by hinge after clearing housing (1007). Needle safety cover includes a pair of concave shields (1050) in a hinged relationship coupled to arm. The concave shields are adapted to at least partially surround the syringe barrel in the un-deployed state. Arm (1006), contained in external housing (1002) is coupled at distal end (1008) to bias (1010), and includes latch (1024) configured to engage latch shelf (1012). When the latch is engaged with the latch shelf the needle (915) is exposed and needle safety cover is positioned adjacent the lower housing. During deployment, concave shields are urged by bias means toward the needle tip until the shields clear the lower housing. A camming surface (1009) guides each shield during deployment. After clearing the lower housing, the shields collapse about hinge (1022) to encase at least the tip of the needle. FIG. 11A is a detail view of cam follower (1032) deposed into its final position by vertical surface (1090). Inclined surface (1080) provides twisting motion or, alternatively, bias means (1010) is loaded in such a manor that it provides twisting motion when it is freed from vertical camming surface (1009). Offset of vertical surface (1090) and camming surface prevents or reduces retraction of arm (1006) after deployment. As shown in FIGS. 12-12A, locking means, for example, locking tab (1070) and receiving slot (1075), secure the concave shields encasing the needle and prevent the removal of the shields and access to the needle after deployment. Recess (1087) accepts needle tip and further secures shields about needle.

Figures 13, 13A:
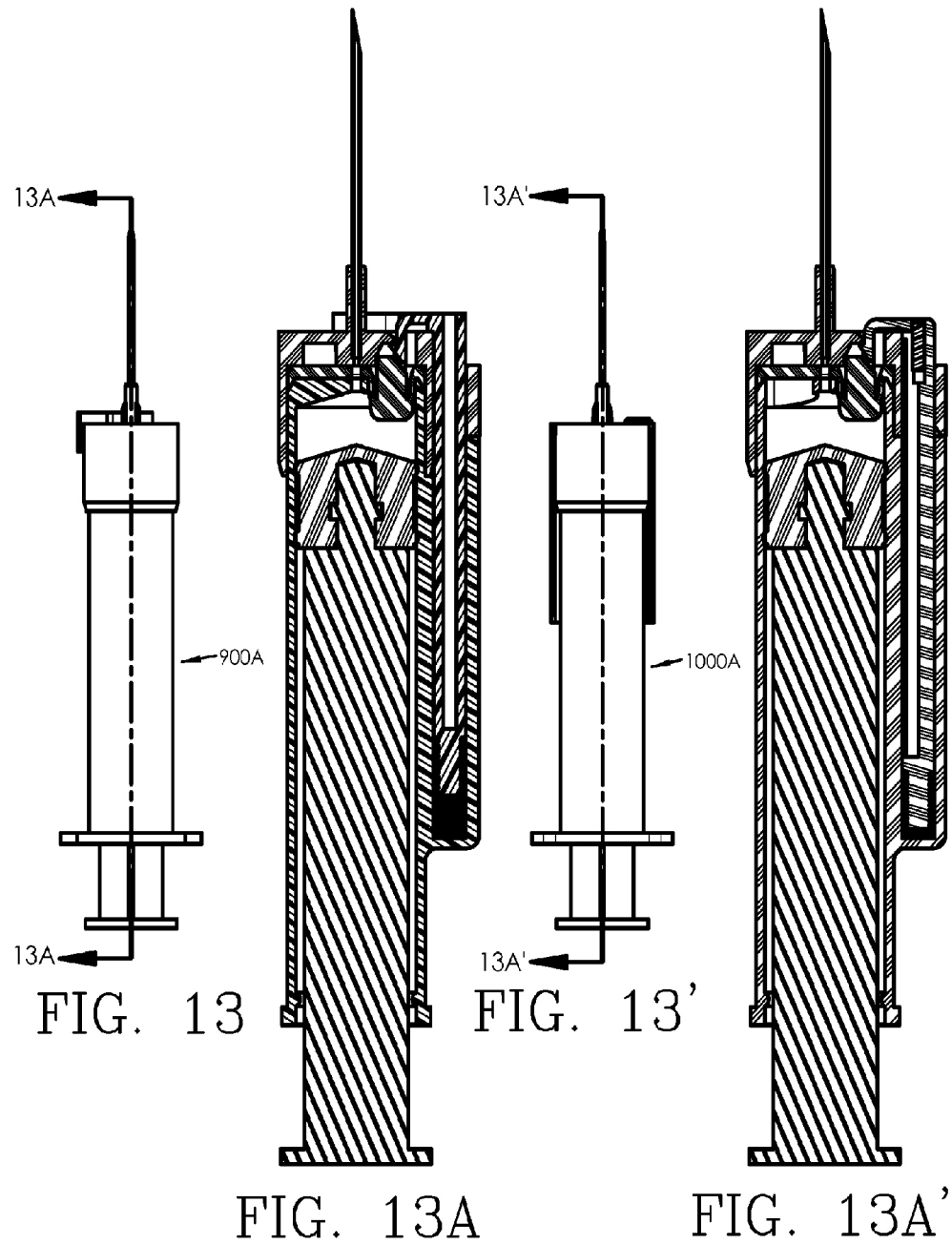
FIGS. 13 and 13A are sectional plane and cross-sectional views, respectively, of an embodiment of FIG. 1 without an access port.

Referring now to FIGS. 13-13A', aspects of the present invention are depicted without the access port. Thus, sectional view of syringe 900A, having needle safety mechanism as shown in FIGS. 2-5C without access port. Likewise, sectional view of syringe 1000A, having needle safety mechanism as shown in FIGS. 6-12A without access port.

Figures 16, 16A:
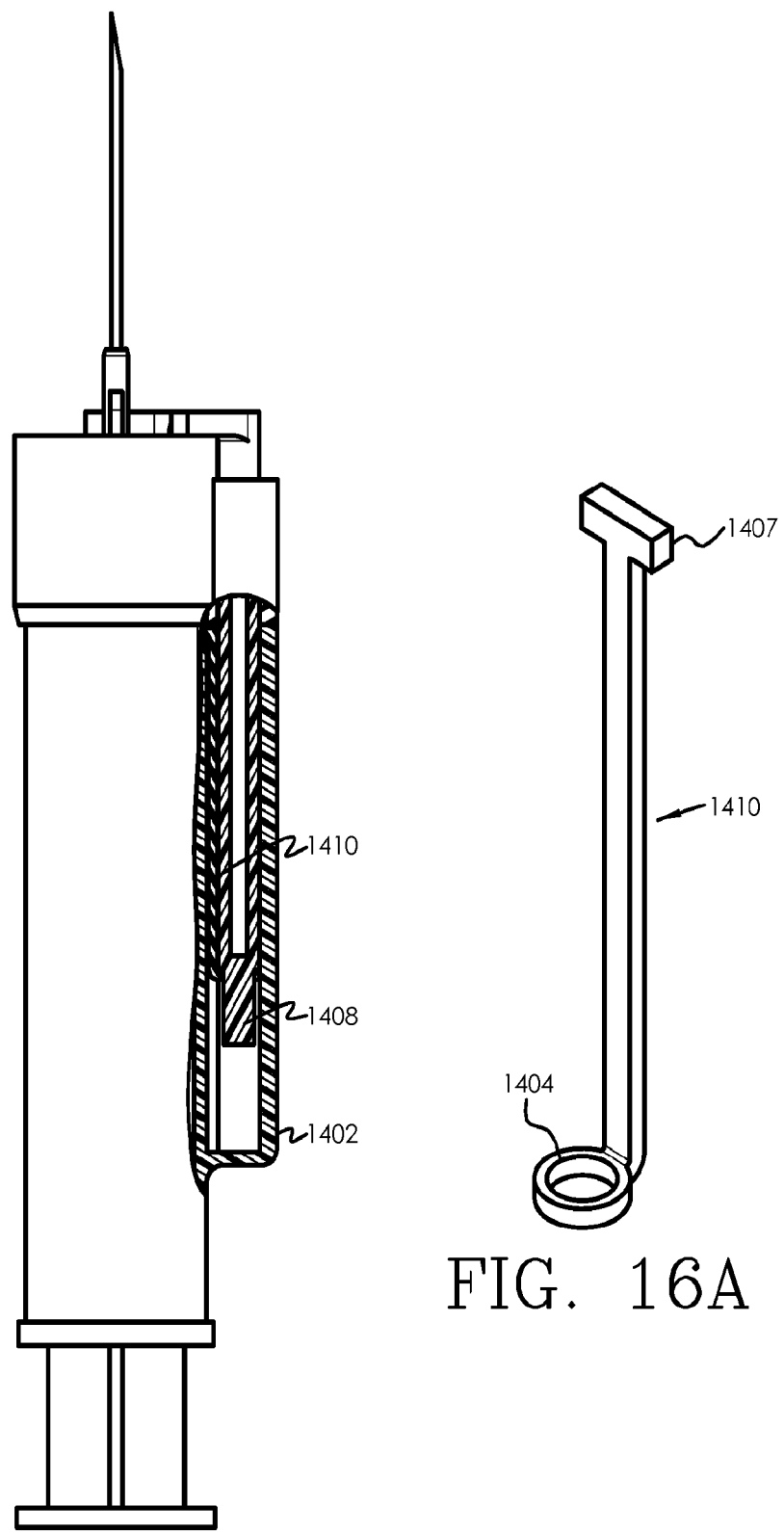
FIG. 16 is a profile view of a partial sectional view of an embodiment disclosed herein with an elastomeric tension spring for deploying for loading the safety mechanism.
FIG. 16A is a perspective view of the elastomeric tension spring of FIG. 16.

Referring now to FIGS. 14-14A, exemplary stored energy bias means are depicted. Thus, FIG. 14-14A depicts deployed safety mechanism comprising an elastomeric compression spring (1300). FIG. 15 depicts an un deployed safety mechanism comprising compressed fluid (999), such as air, as the stored energy bias. FIGS. 16-16A depict an elastomeric tension band (1410) having securing end (1407) anchored to external housing (1402) or syringe barrel, and loop (1404) coupled to arm (1408).

Figure 17:
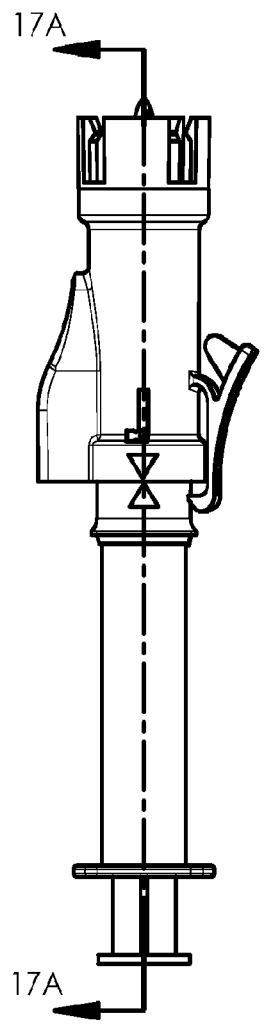
FIGS. 17-17A are sectional plane and partial cross-sectional views of a syringe and vial access device combination embodiment disclosed herein.
Figure 17A:
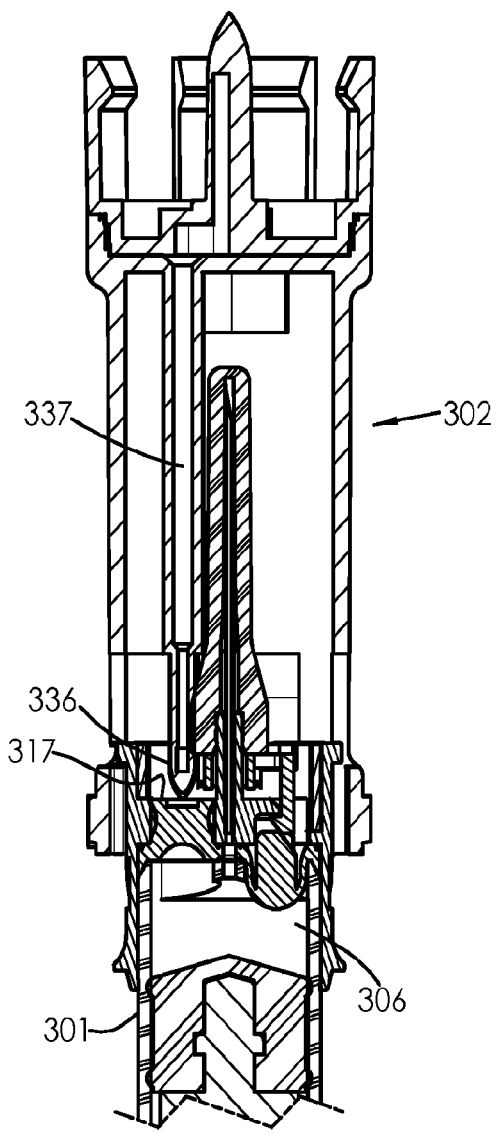
Figure 17A:
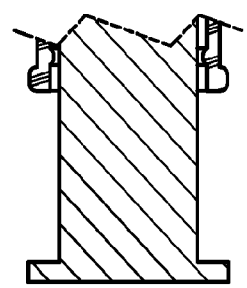
Figure 18:
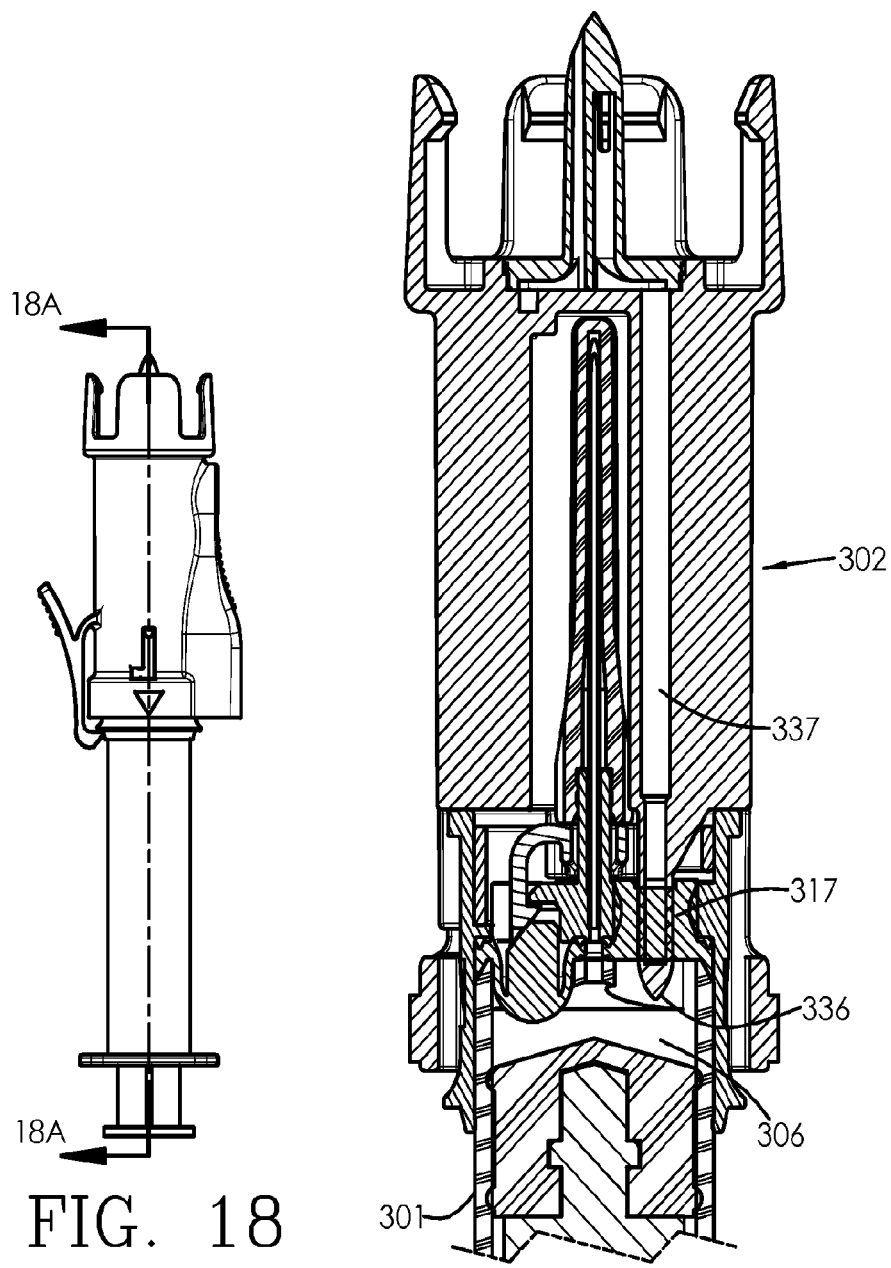
FIGS. 18-18A are sectional plane and partial cross-sectional views of a syringe and vial access device combination embodiment disclosed herein.
Figure 18A:
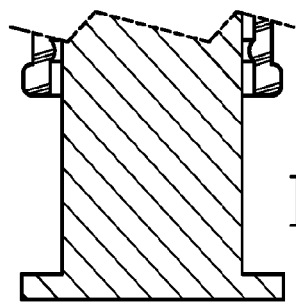

FIG. 17-17A are sectional plane and cross-sectional views of the combination of vial access device and syringe with needle-stick mechanism in the un-activated pre-access configuration preventing fluid communication between the syringe accessing member and the syringe. As shown, syringe accessing member (336) is aligned with access port (317) of the syringe for piercing. FIGS. 18-18A are sectional plane and cross-sectional views of the combination of vial access device and syringe with needle-stick mechanism in the activated bypass access configuration allowing fluid communication between the syringe accessing member and the syringe. As shown, syringe accessing member (336) pierces access port (317) of the syringe allowing for fluid communication between syringe (301) and interconnected conduit (337) of vial access device (302).

Figures 19, 19A:
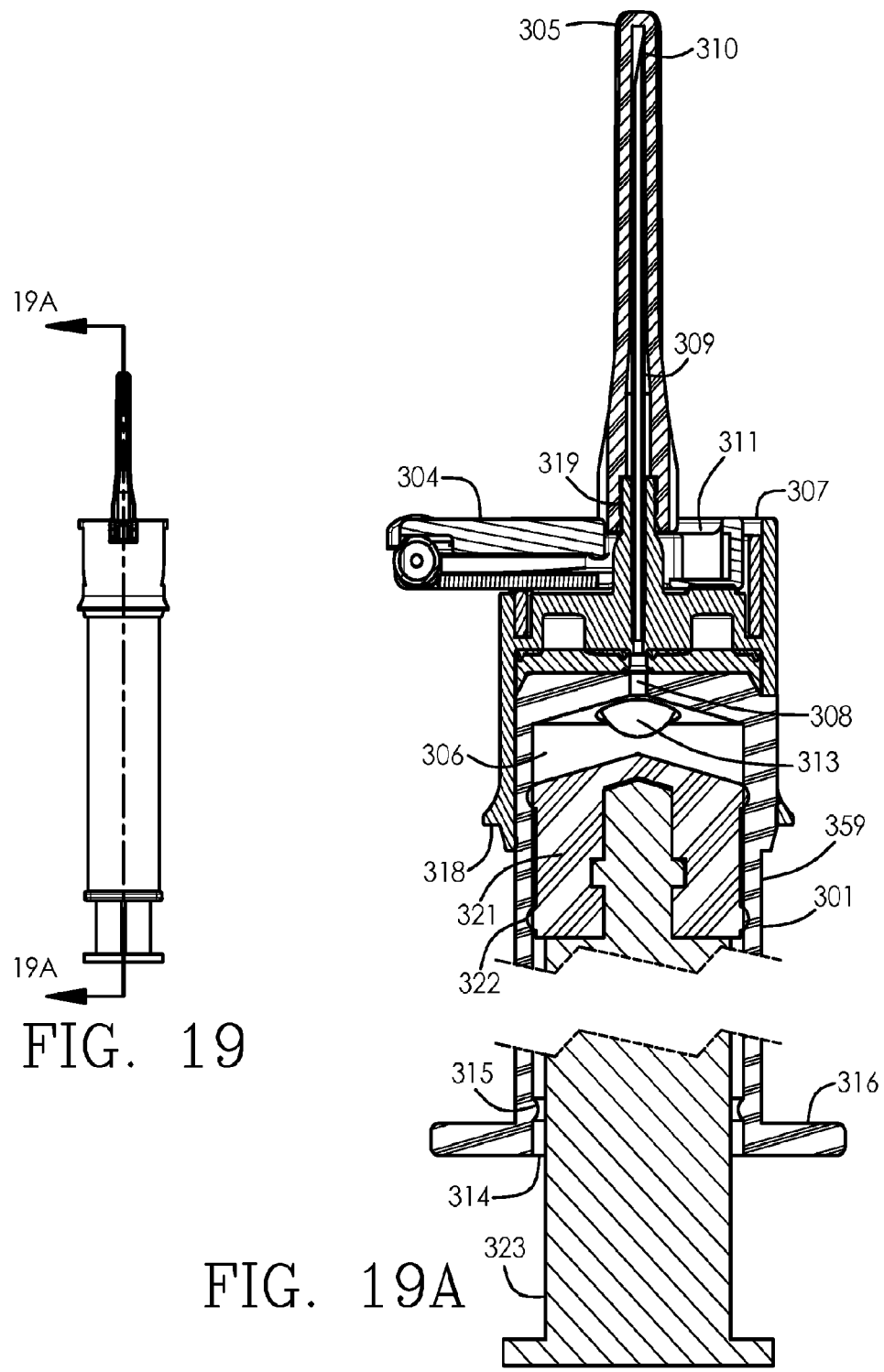

FIGS. 19-20A are sectional plane and cross-sectional views of another embodiment of a syringe with removable needle cap and needle-stick safety mechanism. FIG. 19A depicts syringe (301) with needle cap (305) and needle-stick safety mechanism (304) and attached lower housing (307). Syringe (301) has open end (314) having any number of proximally located retaining means (315) and exterior portion (359) having protruding flanges (316). Syringe (301) comprises elastomeric stopper (321) having any number of seal rings (322) joined to plunger rod (323). Lower housing (307) has inner portion (311) for accepting needle-stick safety mechanism (304) also including latching shelf (312) to secure needle-stick safety mechanism latch (324) in an un-activated state. Lower housing (307) also comprises deformable member (313) and access port (317) allowing for fluid communication with the syringe when pierced by an accessing member and at least one vial access device coupling means (318). Lower housing (307) comprises hub portion (319) allowing for a sealable connection with a needle and/or needle cap. Lower housing (307) includes alignment means (320). Fluid conduit (308) provides for fluid communication with hollow needle (309) having pointed distal end (310). FIG. 20A depicts latch (324) of a needle-stick safety mechanism in its collapsed, un-deployed configuration, coupled with latching shelf (312) of the lower housing.

Figures 21, 21A:
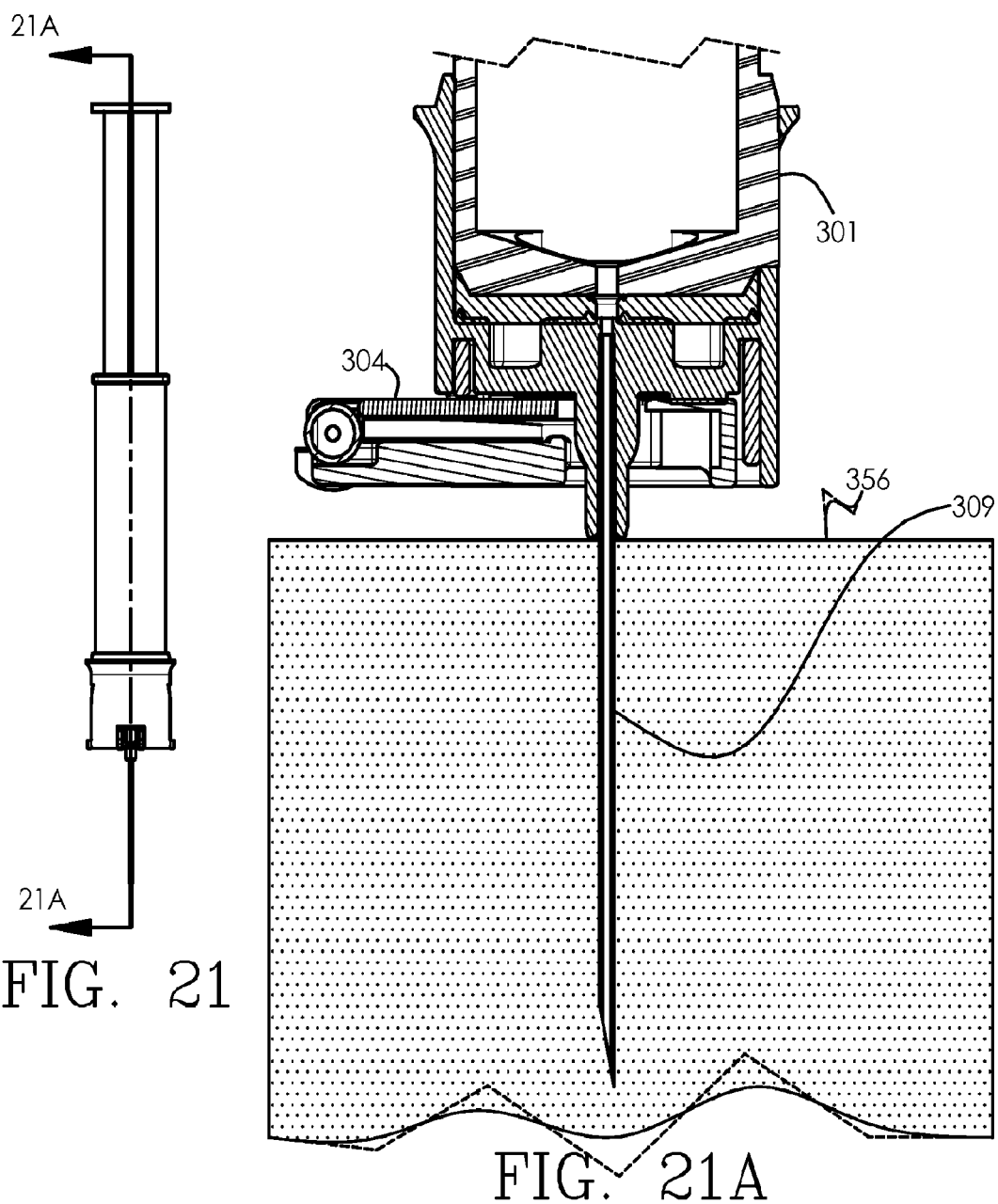
FIGS. 21-21A and 22-22A are sectional plane and partial cross-sectional views, respectively, of a needle-stick safety mechanism embodiment and needle fully inserted into a subject, with plunger in the reward and forward positions, respectively, prior to deployment.
Figures 22, 22A:
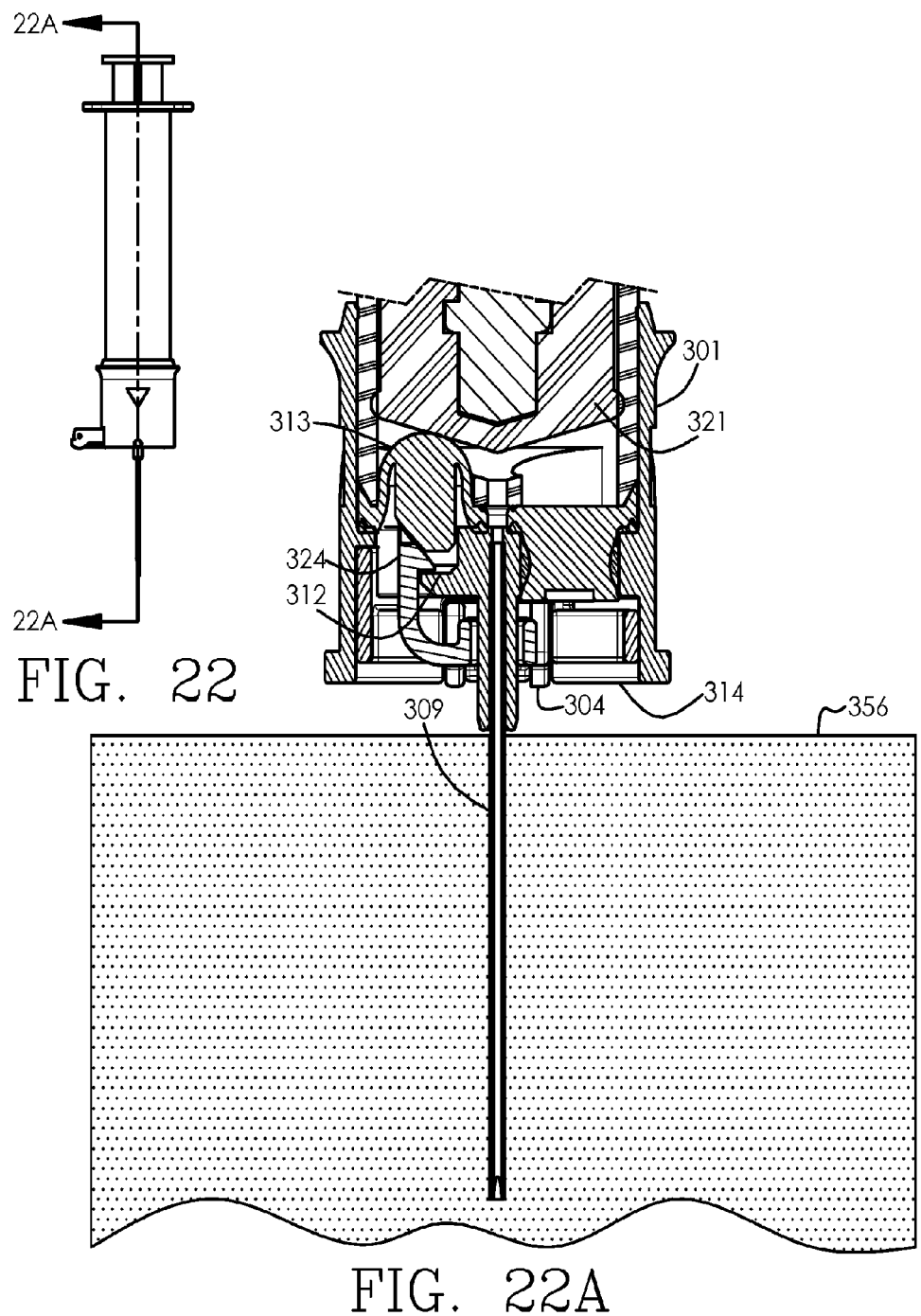

FIGS. 21-22A are sectional plane and cross-sectional views of the embodiment of FIGS. 19-20A depicting the activation of the needle-stick safety mechanism. FIG. 21A shows syringe (301) with needle-stick safety mechanism (304) inserted into skin (356). As syringe stopper (321) approaches second end (314) of the syringe, fluid is expelled through hollow needle (309). When the syringe stopper reaches end-of-stroke, it contacts deformable member (313) releasing latch (324) from latching shelf (312) of the needle-stick safety mechanism, activating and deploying the needle-stick safety mechanism, as shown in FIG. 22A.

Figure 23:
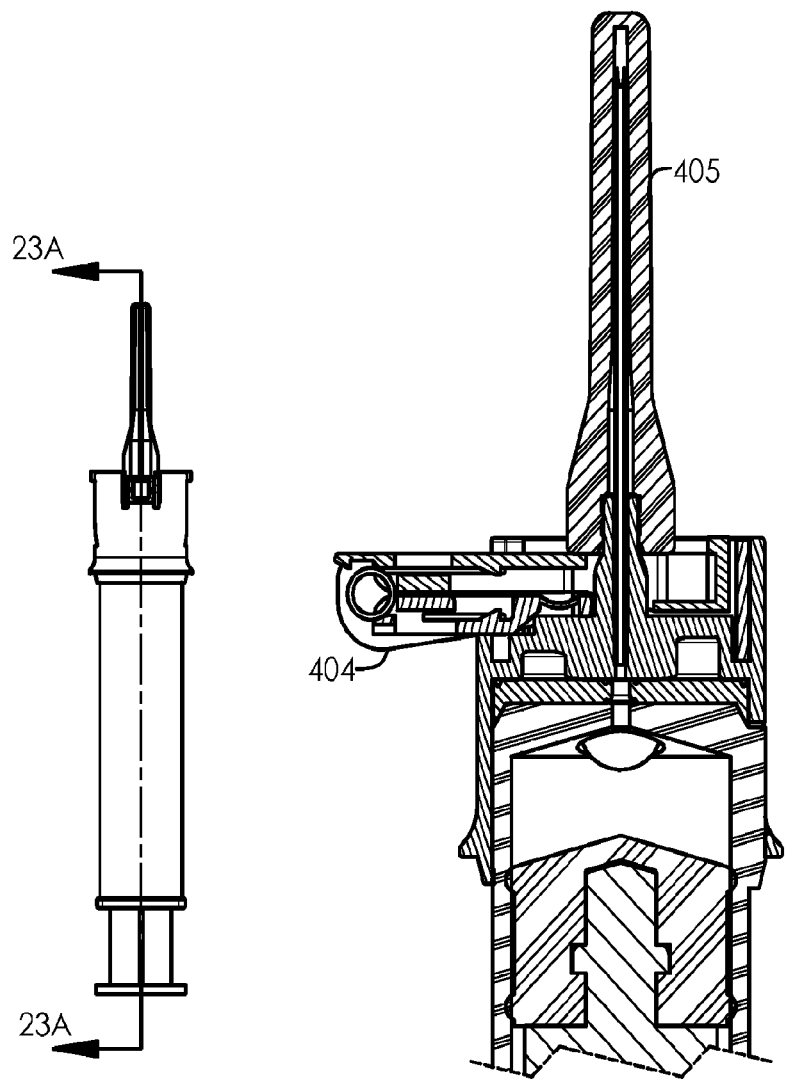
FIGS. 23-23A and 24-24A are sectional plane and partial cross-sectional views, respectively, of a needle-stick safety mechanism embodiment with needle cap.
Figure 23A:
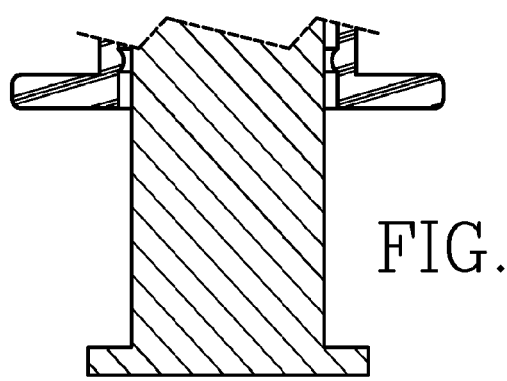
Figure 24:
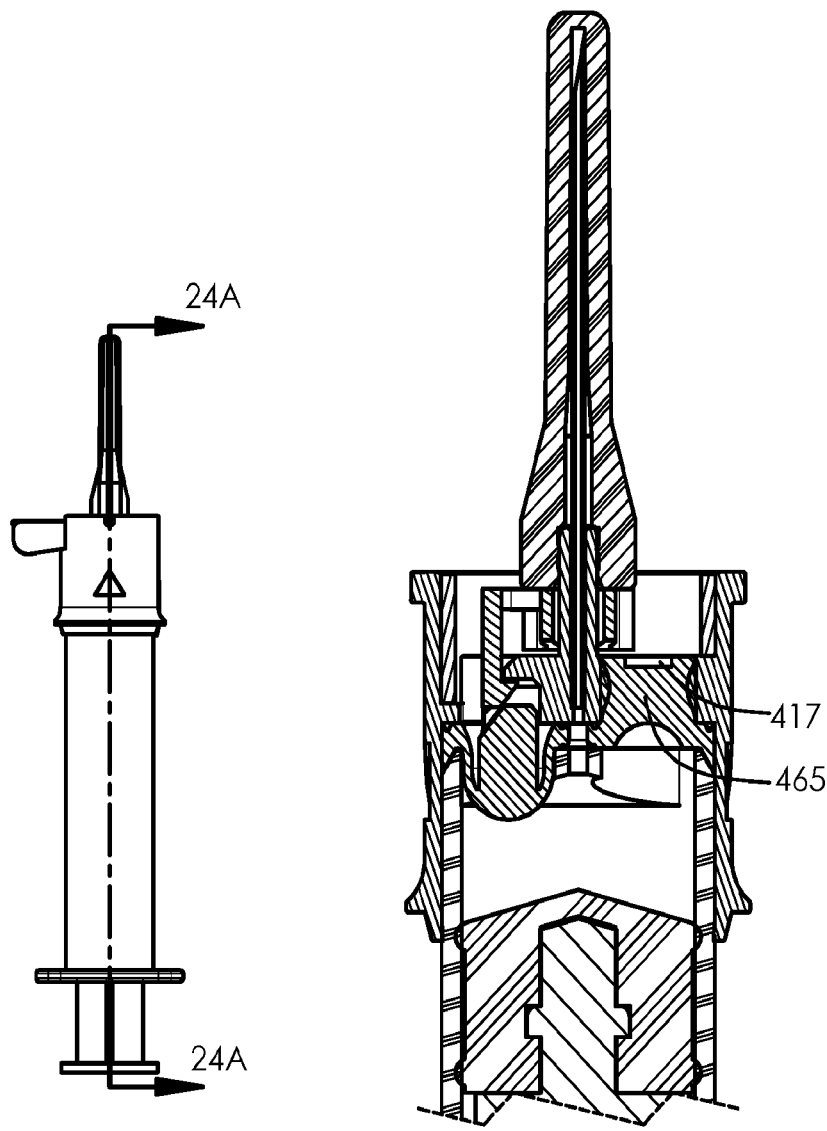
Figure 24A:
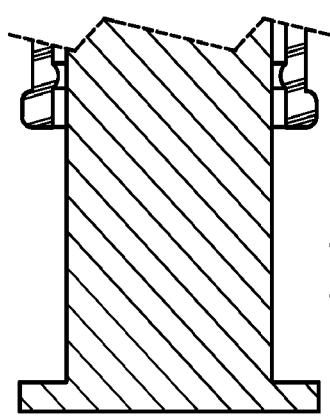
Figures 25, 25A:
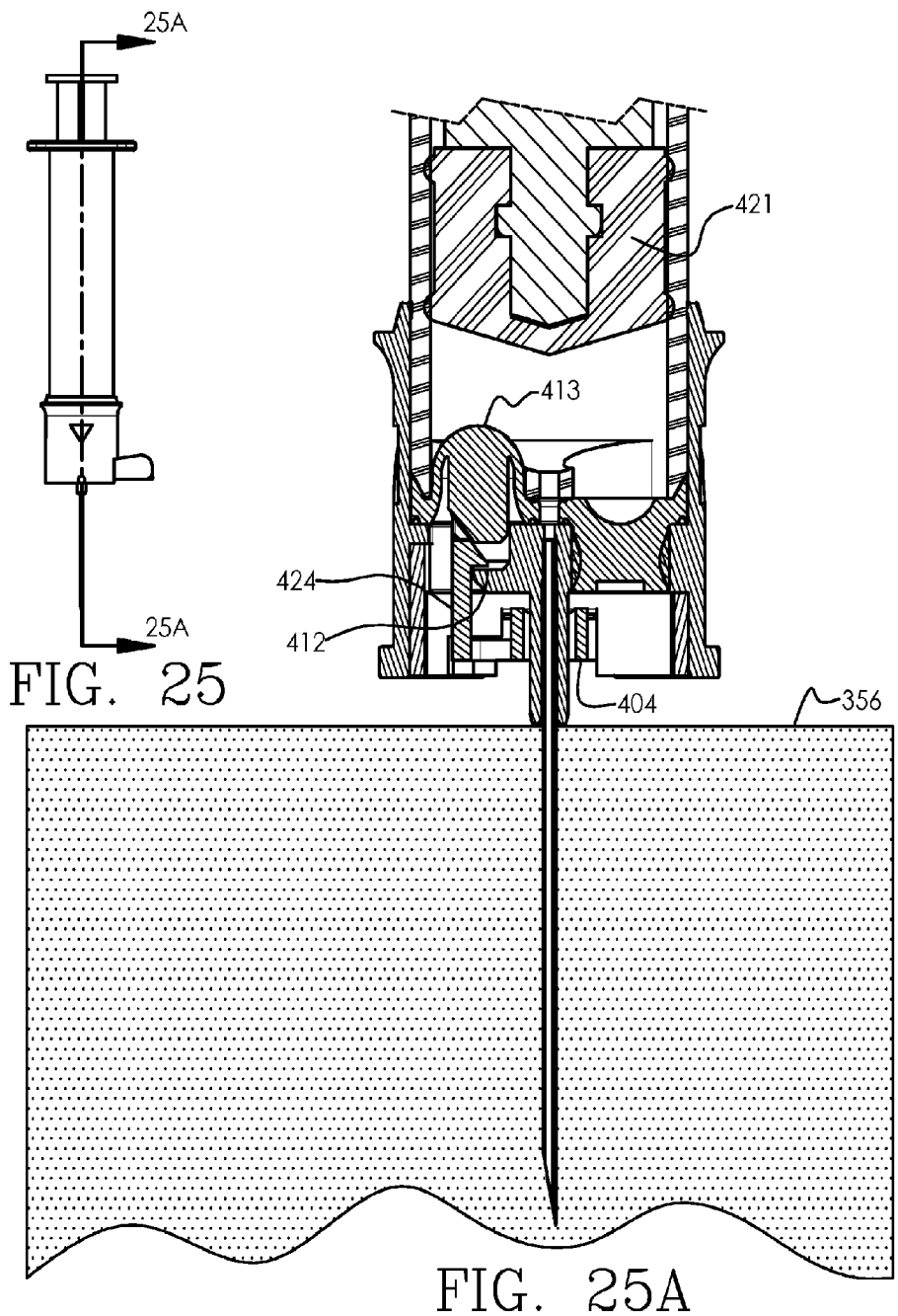
FIGS. 25-25A and 26-26A are sectional plane and partial cross-sectional views of the needle-stick safety mechanism embodiment of FIGS. 23-23A, shown fully inserted into subject, with plunger in the reward and forward positions, respectively, prior to deployment.
Figure 26:
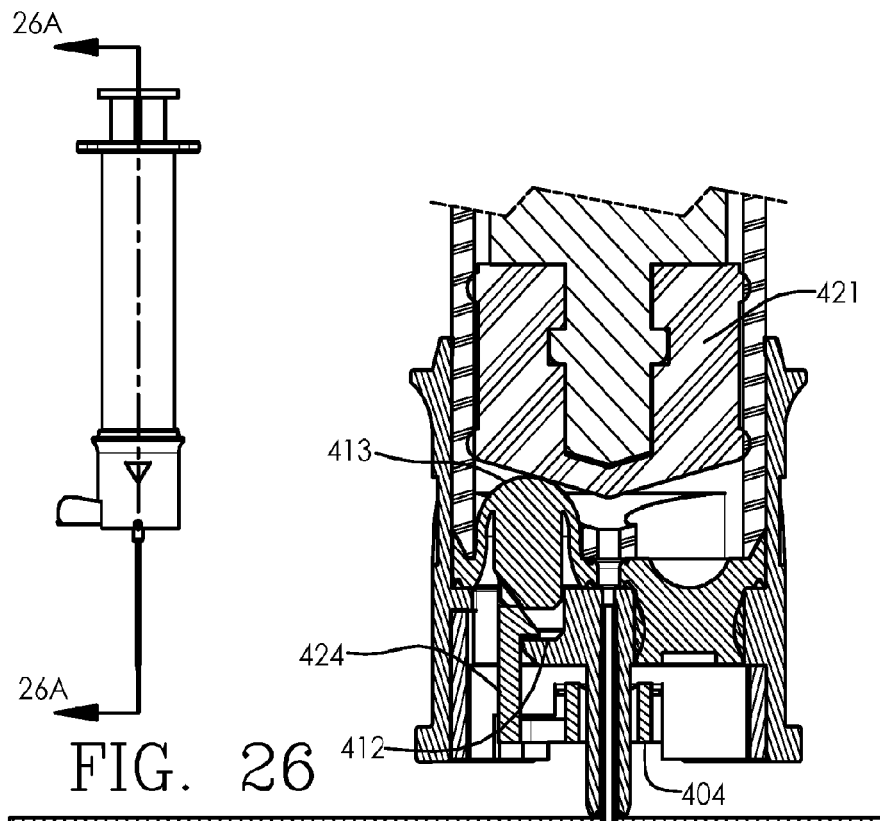
Figure 26A:
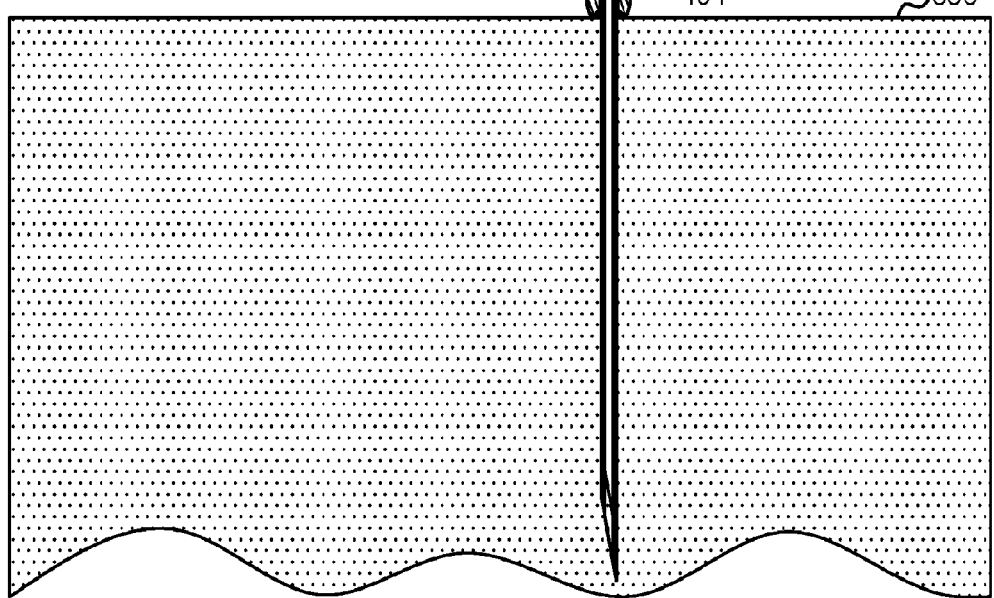
Figure 27:
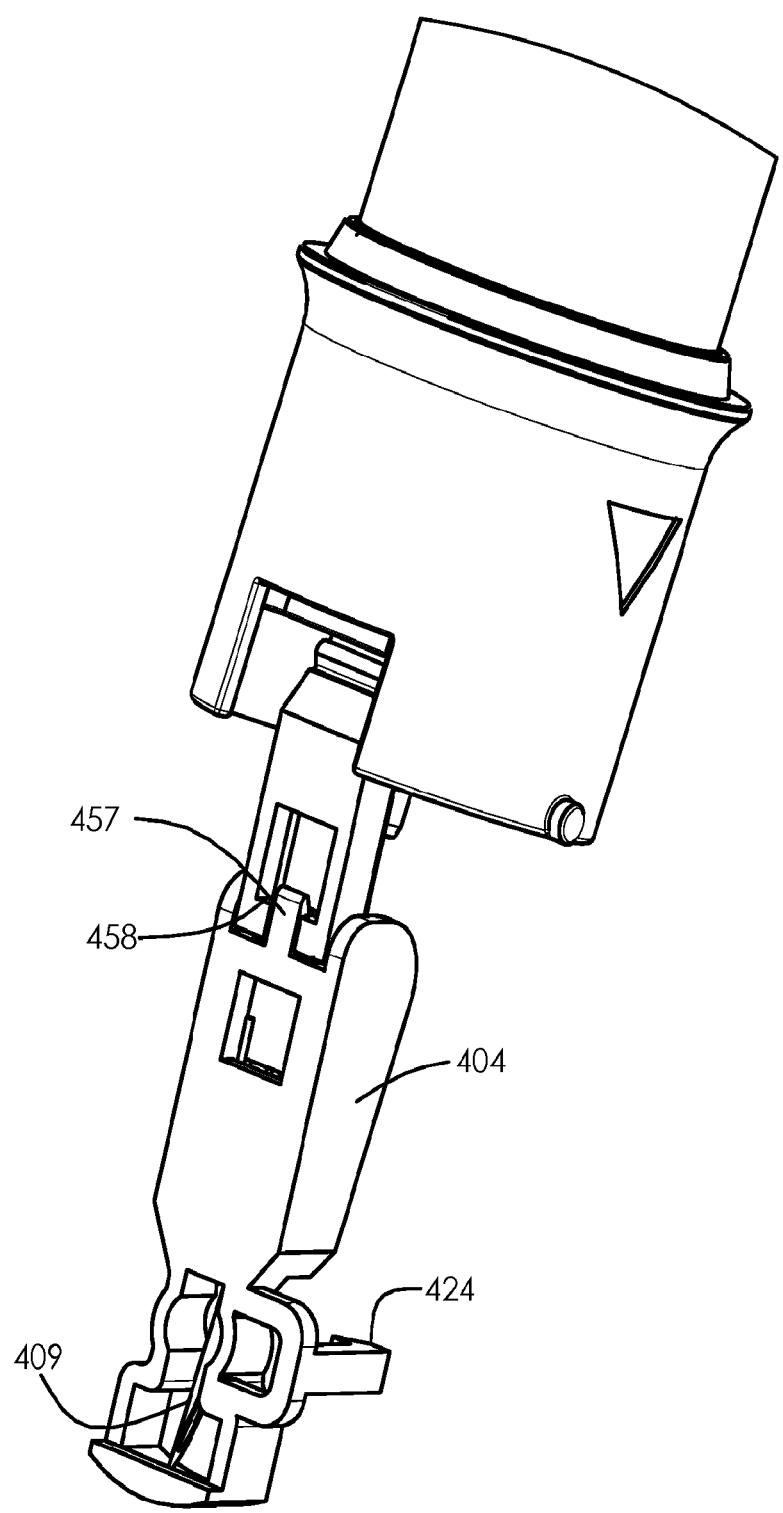
FIG. 27 is a perspective view of the needle-stick safety mechanism embodiment of FIGS. 23-23A, shown in a deployed configuration.

FIGS. 23-27A are sectional plane and cross-sectional views of another embodiment of a syringe with removable needle cap and needle-stick safety mechanism. FIG. 23A depicts needle cap (405) and needle-stick safety mechanism (404); a syringe as described in FIG. 25A depicts access port (417) having alternate geometries (465) preventing coring and/or allow for greater flow rates. The geometries of the access port include, but are not limited to, embossed means, de-bossed means or combinations thereof FIGS. 25-26A and 27 depict the needle-stick safety mechanism (404) sequence of activation and final configuration of FIGS. 23-24A. As syringe stopper (421) reaches end-of-stroke, it contacts deformable member (413) releasing latch (424) from latch shelf (412) of the needle-stick safety mechanism, activating and deploying the needle-stick safety mechanism (404). Locking tab (457) and mating locking shelf (458) prevent the mechanism from collapsing and exposing needle (409).

Figure 29:
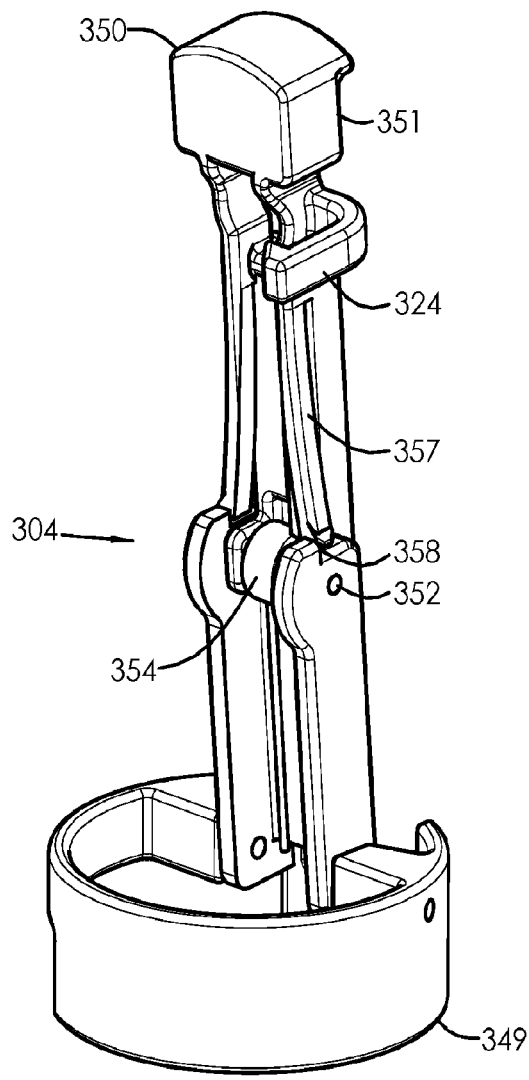
FIGS. 28-29 are perspective views of a needle-stick safety mechanism embodiment disclosed herein shown in an undeployed and deployed configuration, respectively.
Figure 30:
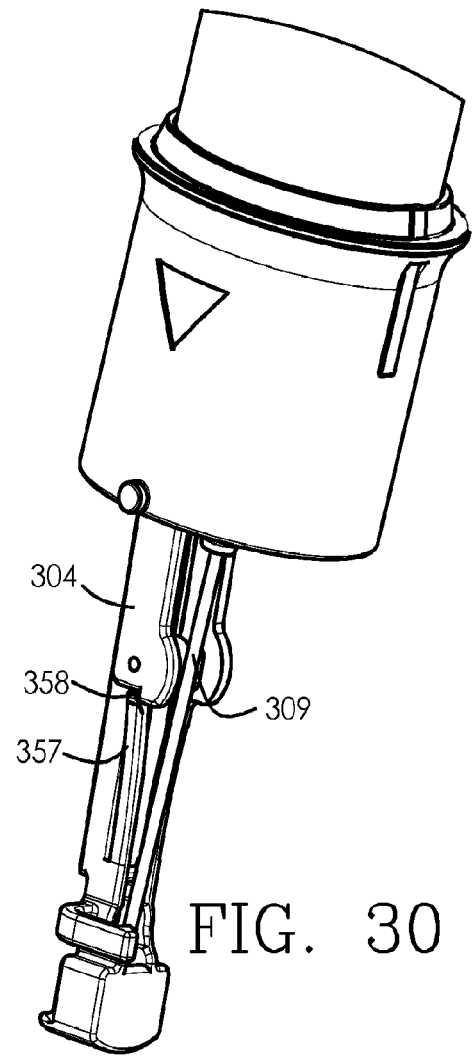
FIG. 30 is a partial perspective view of a fully assembled syringe with needle-stick safety mechanism embodiment disclosed herein in a fully deployed configuration.
Figure 28:
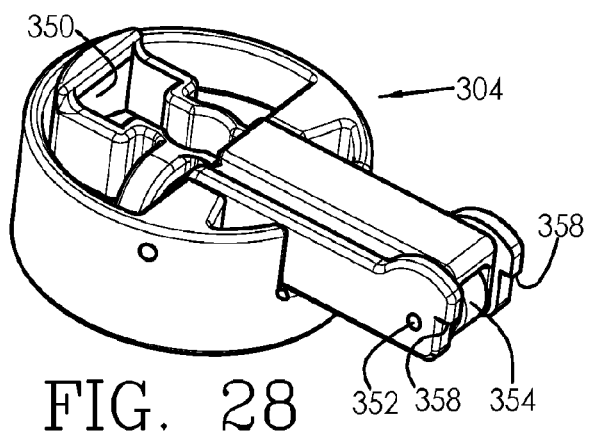

FIGS. 28-30 are perspective views of needle-stick safety mechanism (304) of FIGS. 21-22 shown in its collapsed and deployed configuration, respectively. The hinges and geometries shown allow for the mechanism to collapse upon itself to minimize its overall size. Needle-stick safety mechanism (304) comprises first end (349) for joining to a lowing housing adaptable to a syringe; second end (350) forming a semi-enclosed space (351), at least one hinge (352) between the first and second ends, at least one latch (324) and a torsionally loadable spring element (354). At least one locking tab (357) is loaded so that when the mechanism is extended as shown in FIG. 29, interference with locking shelves (358) prevents rotation about hinge (352). FIG. 30 depicts needle-stick safety mechanism (304) coupled with housing of syringe and including needle.

Figures 31, 32:
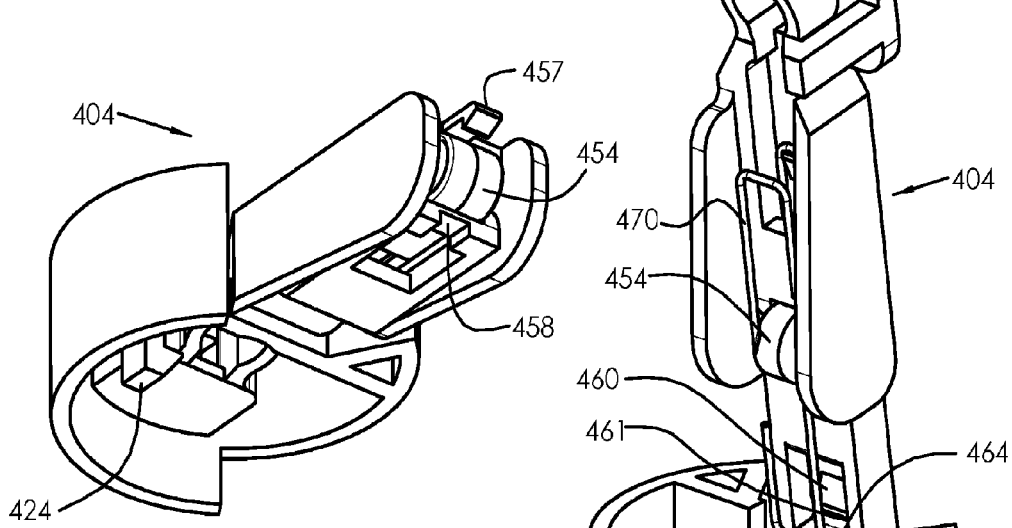
FIG. 31 is a perspective view of a needle-stick safety mechanism embodiment disclosed herein shown in an undeployed configuration.
FIG. 32 is a perspective view of a needle-stick safety mechanism embodiment disclosed herein shown in a collapsed, deployed configuration.

FIGS. 31 and 32 are perspective views of a needle-stick safety mechanism (404) of FIGS. 23-27A shown in the collapsed and deployed configuration, respectively. Locking tab (460) and locking latch (461) are depicted after deployment by stored energy living hinge (464), spring (470) and torsionally loaded member (454). The hinges and geometries may allow for the mechanism to collapse upon itself to minimize its overall size.

While the invention has been described in detail and with reference to specific embodiments thereof, it will be apparent to one skilled in the art that various changes and modifications can be made without departing from the spirit and scope of the invention. As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

We claim:

1. An apparatus comprising:
   a syringe barrel having an open end and an opposite end adapted for a needle, the needle having a tip;
   a needle safety cover displaceable between a un-deployed state wherein the needle safety cover is constrained and the needle exposed, and a deployed state wherein the needle safety cover covers at least the tip of the needle;
   a plunger slidably engaged in the syringe barrel; at least one element securing the needle safety cover in the un-deployed state;
   biasing means urging the needle safety cover from the un-deployed state to a deployed state covering at least a portion of the needle; and a housing coupled to the opposite end of the syringe barrel, the housing comprising a corresponding securing member and a deformable member, the deformable member releasing the at least one element from the corresponding securing member upon receiving a releasing force via the plunger and
   an external housing adjacent the exterior of the syringe barrel, the external housing having an opening, the external housing comprising the biasing means and an arm, the arm coupled to the biasing means at one end and coupled to the needle safety cover at the opposite end.

2. The apparatus of claim 1, wherein the arm provides vertical motion and rotational motion of the needle safety cover during deployment.

3. The apparatus of claim 1, wherein during deployment the needle safety cover avoids contacting the needle.

4. The apparatus of claim 1, wherein the external housing is configured such that the follower is prevented from rotation and reversing after deployment.

5. The apparatus of claim 1, wherein the at least one element securing the needle safety cover is integral with the needle safety cover.

6. The apparatus of claim 1, wherein the needle safety cover rotates about at least a portion of the external housing during deployment from the un-deployed state to the deployed state.

7. The apparatus of claim 1, wherein the needle safety cover comprises a pair of concave shields hingably coupled to the arm.

8. The apparatus of claim 7, wherein the pair of concave shields encases at least the tip of the needle after deployment.

9. A method of preventing blood contact during operation of a needle safety mechanism, the method comprising:

provuding a syringe with a needle, the syringe comprising a needle safety mechanism, the needle safety mechanism deploying a needle safety cover from un-deployed state wherein the cover is constrained and the needle exposed, to a deployed state wherein the cover covers at least the tip of the needle, wherein the needle safety mechanism comprises a plunger slidably engaged in the barrel of the syringe; and at least one element securing the needle safety cover in the un-deployed state, biasing means for urging the needle safety cover from the un-deployed state to a deployed state covering at least a portion of the needle; a housing coupled to the syringe barrel opposite the open end, the housing comprising a corresponding securing member and a deformable member, the deformable member releasing the at least one element from the securing member upon receiving a releasing force via the plunger; and avoiding contact of the needle safety cover with the needle during deployment and an external housing adjacent the exterior of the syringe barrel, the external housing having an opening, the external housing comprising the biasing means and an arm, the arm coupled to the biasing means at one end and coupled to the needle safety cover at the opposite end.

10. The method of claim 9, wherein the arm provides vertical and rotational motion of the needle safety cover during deployment and the arm is configured such that the arm is prevented from rotation and reversing after deployment.

11. The method of claim 9, wherein the at least one element securing the needle safety cover is integral with the needle safety cover.

12. The method of claim 9 wherein the needle safety cover rotates at least partially about the external housing during deployment from the un-deployed state to the deployed state and covers at least the tip of the needle after deployment.

13. The method of claim 9, wherein the needle safety cover comprises a pair of concave shields hingably coupled to the arm, the pair of concave shields encasing at least the tip of the needle in the deployed state.

* * * * *